United States Patent
Jacobson

(10) Patent No.: US 9,388,407 B2
(45) Date of Patent: *Jul. 12, 2016

(54) METHODS AND DEVICES FOR NUCLEIC ACID SYNTHESIS

(71) Applicant: Gen9, Inc., Cambridge, MA (US)

(72) Inventor: Joseph Jacobson, Newton, MA (US)

(73) Assignee: Gen9, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,683

(22) Filed: Mar. 31, 2014

(65) Prior Publication Data

US 2015/0065393 A1 Mar. 5, 2015

Related U.S. Application Data

(62) Division of application No. 13/038,714, filed on Mar. 2, 2011, now Pat. No. 8,716,467.

(60) Provisional application No. 61/310,100, filed on Mar. 3, 2010.

(51) Int. Cl.
C12N 15/10 (2006.01)
C12M 1/00 (2006.01)
C12P 19/34 (2006.01)

(52) U.S. Cl.
CPC ............. *C12N 15/1068* (2013.01); *C12M 1/00* (2013.01); *C12P 19/34* (2013.01)

(58) Field of Classification Search
None
See application file for complete search history.

(56) References Cited

U.S. PATENT DOCUMENTS

| | | |
|---|---|---|
| 4,500,707 A | 2/1985 | Caruthers et al. |
| 4,725,677 A | 2/1988 | Koster et al. |
| 5,047,524 A | 9/1991 | Andrus et al. |
| 5,143,854 A | 9/1992 | Pirrung et al. |
| 5,288,514 A | 2/1994 | Ellman |
| 5,384,261 A | 1/1995 | Winkler et al. |
| 5,510,270 A | 4/1996 | Fodor et al. |
| 5,527,681 A | 6/1996 | Holmes |
| 5,541,061 A | 7/1996 | Fodor et al. |
| 5,639,603 A | 6/1997 | Dower et al. |
| 5,700,637 A | 12/1997 | Southern |
| 5,770,358 A | 6/1998 | Dower et al. |
| 6,375,903 B1 | 4/2002 | Cerrina et al. |
| 6,800,439 B1 | 10/2004 | McGall et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,911,132 B2 | 6/2005 | Pamula et al. |
| 7,323,320 B2 | 1/2008 | Oleinikov |
| 7,563,600 B2 | 7/2009 | Oleinikov |
| 2002/0081582 A1 | 6/2002 | Gao et al. |
| 2003/0047688 A1 | 3/2003 | Faris et al. |
| 2003/0068633 A1 | 4/2003 | Belshaw et al. |
| 2003/0171325 A1 | 9/2003 | Gascoyne |
| 2004/0185484 A1 | 9/2004 | Costa et al. |
| 2006/0054503 A1 | 3/2006 | Pamula et al. |
| 2007/0281309 A1 | 12/2007 | Kong |
| 2008/0274513 A1 | 11/2008 | Shenderov et al. |
| 2009/0087840 A1 | 4/2009 | Baynes et al. |

FOREIGN PATENT DOCUMENTS

| | | |
|---|---|---|
| EP | 1205548 | 5/2005 |
| WO | 9000626 | 1/1990 |
| WO | 9942813 | 8/1999 |
| WO | 0188173 | 11/2001 |
| WO | 0224597 | 3/2002 |
| WO | 03040410 | 5/2003 |
| WO | 03046223 | 6/2003 |
| WO | 03064026 | 8/2003 |
| WO | 03064027 | 8/2003 |
| WO | 03064699 | 8/2003 |
| WO | 03065038 | 8/2003 |
| WO | 03066212 | 8/2003 |
| WO | 03100012 | 12/2003 |
| WO | 2004002627 | 1/2004 |
| WO | 2004090170 | 1/2004 |
| WO | 2004024886 | 3/2004 |
| WO | 2004029586 | 4/2004 |
| WO | 2004031351 | 4/2004 |
| WO | 2004031399 | 4/2004 |
| WO | 2005059096 | 6/2005 |
| WO | 2005071077 | 8/2005 |
| WO | 2006044956 | 4/2006 |

(Continued)

OTHER PUBLICATIONS

Fair, Microfluid Nanofluid, 2007, vol. 3, pp. 245-281.*
Pham et al., Biotechniques, 1998, pp. 206-208.*
Beer, N., et al., "On-chip, real time single-copy polymerase chain reaction in picoliter droplets," Analytical Chemistry, 79(22): 8471-8475, (Nov. 15, 2007).
Binkowski B.F. et al., "Correcting errors in synthetic DNA through consensus shuffling" Nucl. Acids Res., vol. 33, No. 6, e55, 2005.
Blanchard, A., "Synthetic DNA Arrays," Genetic Engineering, 20:111, Plenum Press, (1998).
Carr, P., et al., "Protein-mediated error correction for de novo DNA synthesis," Nucleic Acids Res., 32(20): e162 (9 pages), (2004).
Cho, S., et al. "Creating, transporting, cutting and merging liquid droplets by electrowetting-based actuation for digital microfluidic circuits." J. of Microelectromechanical Systems, 12(1):70-80, (Feb. 2003).

(Continued)

*Primary Examiner* — Michele K Joike
*Assistant Examiner* — Mindy G Brown
(74) *Attorney, Agent, or Firm* — Greenberg Traurig, LLP; Fang Xie; Natalie Salem

(57) ABSTRACT

Disclosed are devices and methods to synthesize polynucleotides and libraries of polynucleotides such as libraries of oligonucleotides. In exemplary embodiments, the device includes a support having a plurality of features. Each feature contains a plurality of oligonucleotides. Within each feature, each of the plurality of oligonucleotides includes an identical predetermined subunit sequence of X nucleosides and a degenerate sequence of Y nucleosides. A predetermined combination of a subset of the features can be used to produce a polynucleotide having a predetermined sequence of Z nucleosides.

18 Claims, 10 Drawing Sheets

(56) References Cited

FOREIGN PATENT DOCUMENTS

| | | |
|---|---|---|
| WO | 2006076679 | 7/2006 |
| WO | 2008024319 | 2/2008 |
| WO | 2010025310 | 3/2010 |
| WO | 2011066186 | 3/2011 |
| WO | 2011056872 | 5/2011 |
| WO | 2011066185 | 6/2011 |

OTHER PUBLICATIONS

Duggan, D., et al., "Expression profiling using cDNA microarrays," Nat. Genet. 21:10-14, (Jan. 1999).

Fair, R., "Digital microfluidics: is a true lab-on-a-chip possible?" Microfluid Nonofluid, 3:245-281, (2007).

Fidalgo, L., et al., "Surface induced droplet fusion in microfluidic devices," Lab on Chip, 7(8)984-986, (2007).

Grifith, E. and Aklella, S. "Coordinating Multiple droplets in Planar Array Digital Microfluidics Systems," The International Journal of Robotics Research, 24(11):933-949, (Nov. 2005).

Gulati, S., et al., "Opportunities for microfluidic technologies in synthetic biology," J.R. Soc. Interface, 6:S493-S506, (2009).

Haeberle, S. and Zengerle, R.,"Microfluidic platforms for lab-on-chip applications," Lab on a Chip, 7(9):1094-1110, (2007).

Kelly, B., et al., "Miniaturizing chemistry and biology in microdroplets," Chem. Commun., 1773-1788, (2007).

Kong, D., et al., "Parallel gene synthesis in a microfluidic device," Nucleic Acids Research, 35(8):e61 (9 pages), (2007).

Liu, Y, et al., "DNA ligation of ultramicrovolume using EWOD microfluidic system with coplanar electrodes: DNA ligation of ultramicrovolume using a EWOD microfluidic system," J. of Micromechanics and Microengineering, 18 (4):45017 (7 pages), (2008).

McGall, G., et al., "Light-directed synthesis of high-density oligonucleotide arrays using semiconductor photoresists," Proc. Natl. Acad. Sci. USA, 93:13555-13560, (Nov. 26, 1996).

Mir K. U. et al. "Sequencing by cyclic ligation and cleavage (CycLic) directly on a microarray captured template". Nucl. Acids Res. vol. 37, No. 1, e5, 2008.

Pham et al., "Sticky-End PCR: New Method for Subcloning", BioTechniques, vol. 25, pp. 206-208, 1998.

Richmond, K., et al., "Amplification and assembly of chip-eluted DNA (AACED): a method for high-throughput gene synthesis," Nucleic Acids Res., 32(17):5011-5018, (2004).

Shabarova, Z., et al., "Chemical ligation of DNA: the first non-enzymatic assembly of a biologically active gene," Nuc. Acids Res., 19(15):4247-51, (1991).

Stekel, D., "Microarrays: making them and using them in microarray bioinformatics," Cambridge University Press, (10 pages), (2003).

Teh, S-Y, et al., "Droplet microfluidics," Lab on Chip, 8(2), (2008).

Tian, J., et al., "Accurate multiplex gene synthesis from programmable DNA microchips," Nature, 432:1050-1054, (Dec. 23/30, 2004).

Xu, Y. and Kool, E., "A Novel 5'-Iodonucleoside allows efficient nonenzymatic ligation of single-stranded and duplex DNAs," Tetrahedron Lett., 38(32):5595-8, (Aug. 11, 1997).

Xu, Y. and Kool, E., "High sequence fidelity in a non-enzymatic DNA autoligation reaction," Nuc. Acids Res., 27 (3):875-81, (1999).

Xu, Y., et al., "Nonenzymatic autoligation in direct three-color detection of RNA and DNA point mutations," Nat. Biotech., 19:148-52, (Feb. 2001).

Zhang, C., et al., "PCR microfluidic devices for DNA amplification," Biotechnology Advances, 24(3):243-284, 2006.

Zhou, X., et al., "Microfluidic picoarray synthesis of oligodeoxynucleotides and simultaneous assembling of multiple DNA sequences," Nucleic Acids Res., 32(18): 5409-5417, (2004).

Zielke, P. and Szymczyk, J., "Experimental investigation of the motion and deformation of droplets on surfaces with a linear wettability gradient," Eur. Phys. J. Special Topics, 166:155-158, (Jan. 2009).

Office Action in U.S. Appl. No. 13/038,714 dated Jan. 25, 2013.

Office Action in U.S. Appl. No. 13/038,714 dated Sep. 23, 2013.

\* cited by examiner

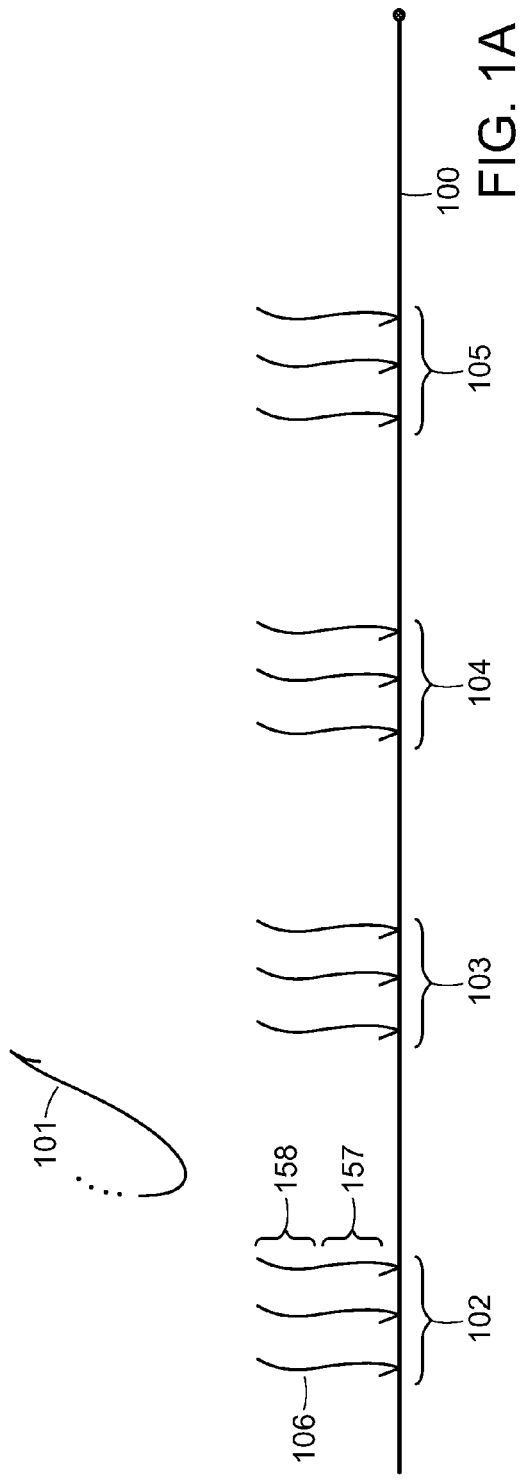
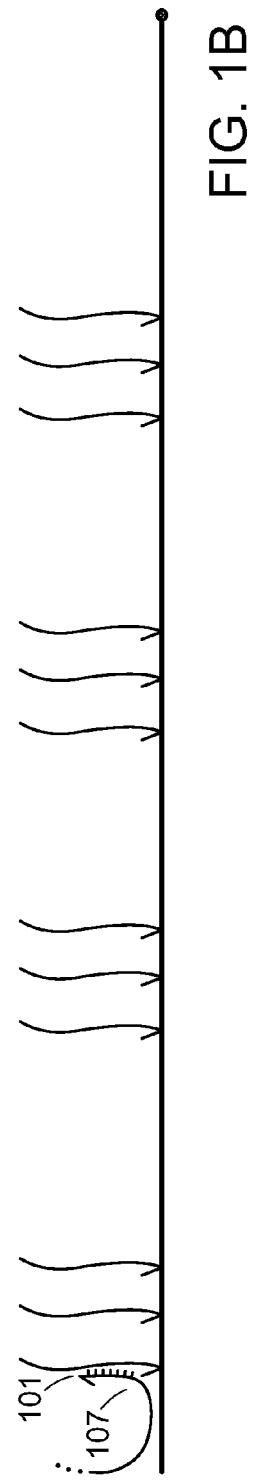

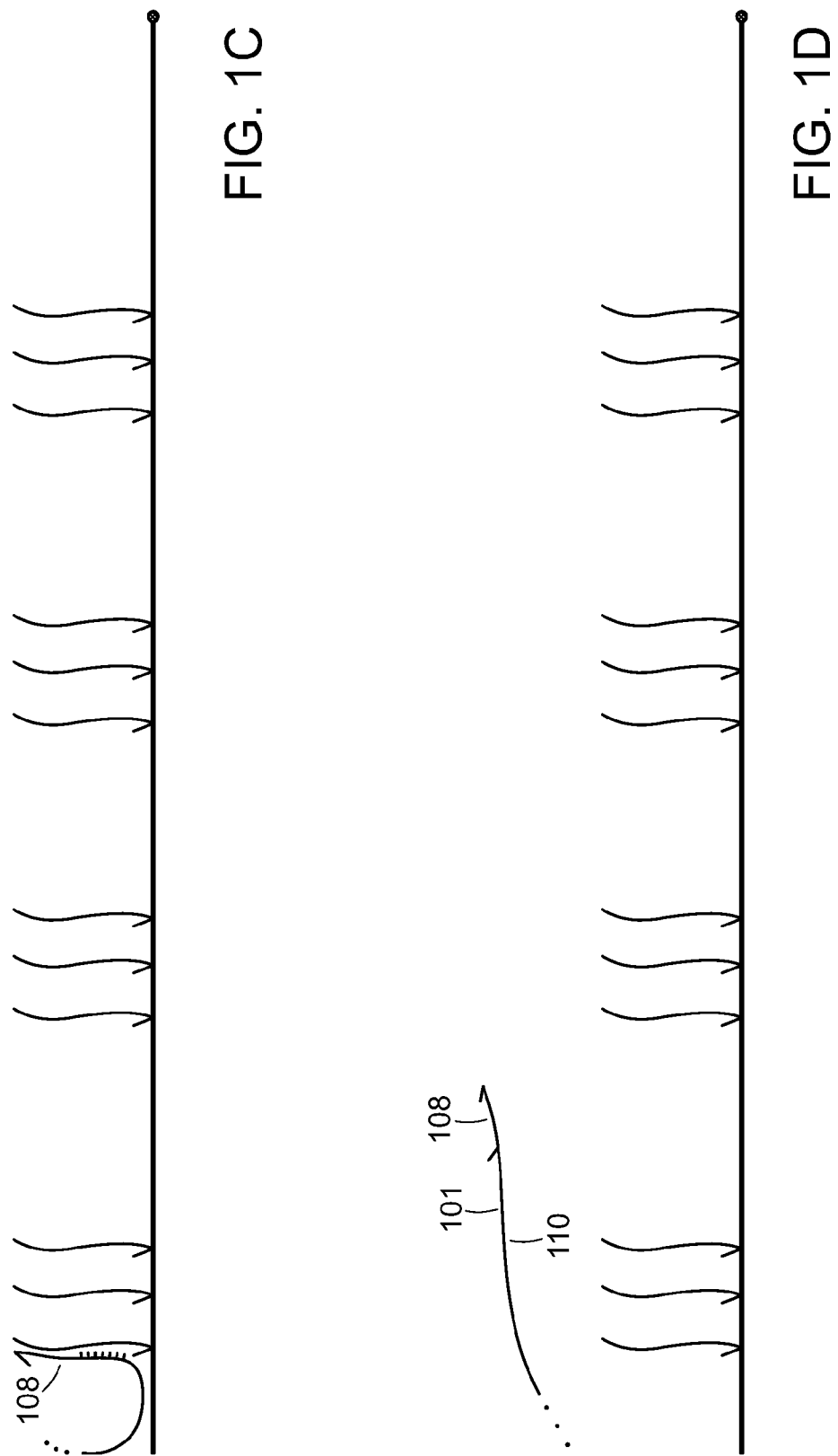

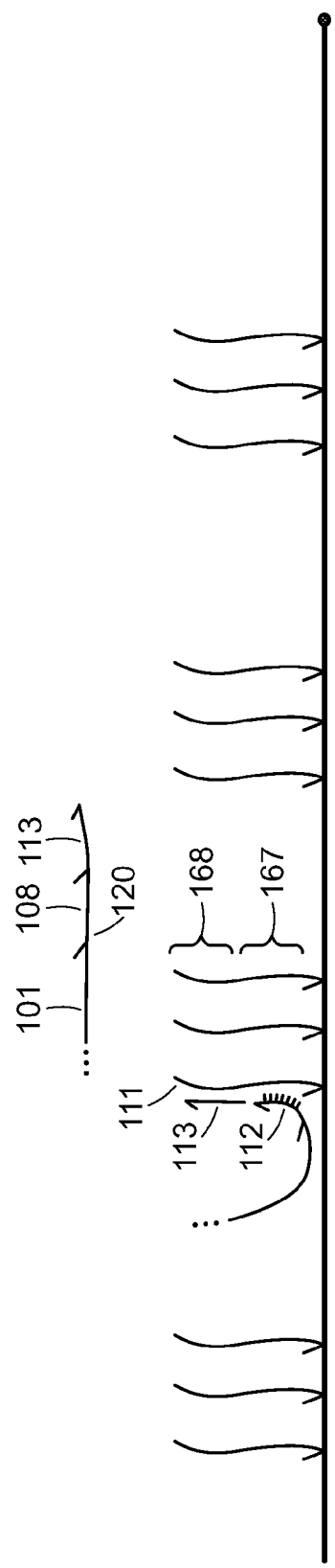
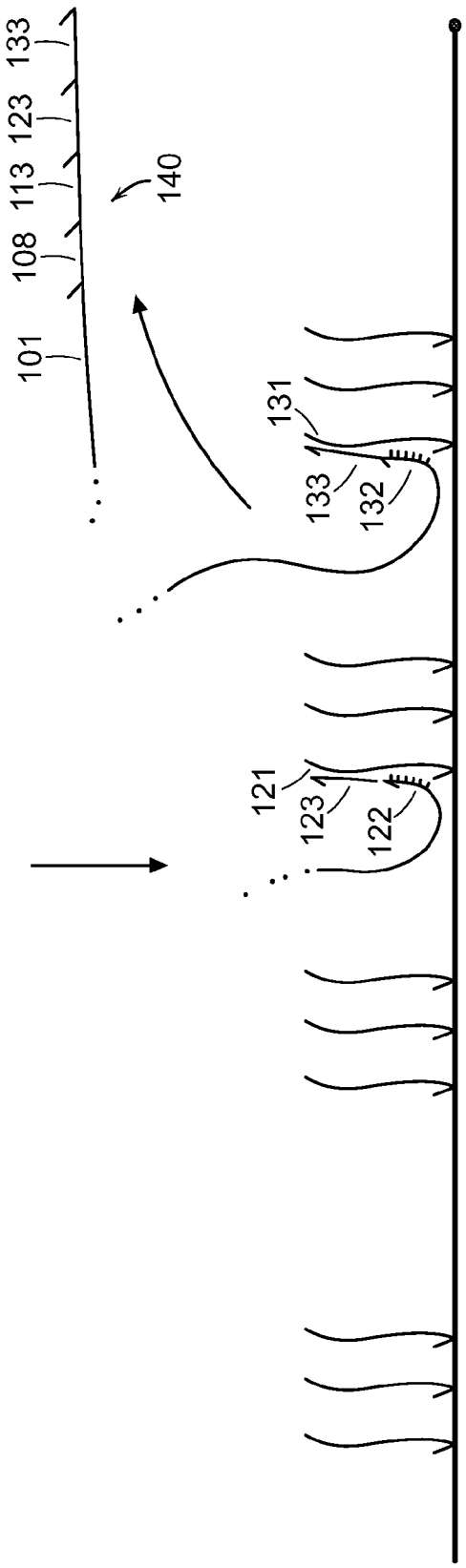

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(15)
<223> OTHER INFORMATION: n is a, c, g, or t

<400> SEQUENCE: 1
agtcannnnn nnnnn                                                15
```

```
<210> SEQ ID NO 2
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(11)
<223> OTHER INFORMATION: n is a, c, g, or t
<220> FEATURE:
<221> NAME/KEY: misc_feature
<222> LOCATION: (12)..(16)
<223> OTHER INFORMATION: PolyA linker region

<400> SEQUENCE: 2
gtactnnnnn naaaaa                                                16

<210> SEQ ID NO 3
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: n is a, c, g, or t

<400> SEQUENCE: 3
nnnnnnagta c                                                     11
```

METHODS AND DEVICES FOR NUCLEIC ACID SYNTHESIS

RELATED APPLICATIONS

This application is a divisional of U.S. patent application Ser. No. 13/038,714, filed Mar. 2, 2011, now U.S. Pat. No. 8,716,467, which claims priority to and the benefit under 35U.S.C. §119(e) of U.S. Provisional Application No. 61/310,100, filed Mar. 3, 2010,the disclosures of all of which are herein incorporated by reference in their entireties.

FIELD OF THE INVENTION

Devices and methods provided herein relate to the automated synthesis of polynucleotides and libraries of polynucleotides. More particularly, the devices and methods are useful for performing synthesis of oligonucleotides. In some embodiments, the devices provide a universal, combinatorial array for synthesizing oligonucleotides having any desired sequence.

BACKGROUND

Synthetic biopolymers such as oligonucleotides play a pivotal role in many fields such as molecular biology, forensic science, and medical diagnostics. Oligonucleotides, in particular, have become indispensable tools in modern biotechnology. Oligonucleotides are being used in a wide variety of techniques, ranging from diagnostic probing methods, PCR, antisense inhibition of gene expression to nucleic acid assembly. This widespread use of oligonucleotides has led to an increasing demand for rapid, inexpensive and efficient methods for synthesizing oligonucleotides. Various types of microarray manufacturing devices and technologies have been described e.g. combinatorial array, ink-jetting, direct surface printing approaches have been extensively described. Most of theses technologies use numerous valves and tubes and other fluid handling components. As such a need remains for a quick, cost effective, scalable oligonucleotide synthesis device able to generate high quality oligonucleotides suitable for an array of applications.

SUMMARY OF THE INVENTION

Aspects of the technology provided herein relate to devices and methods for synthesizing polynucleotides. Aspects of the invention relate to devices and methods for the synthesis of a plurality of polynucleotides and/or libraries of polynucleotides on a solid support. In one aspect of the invention, a device for synthesizing at least one polynucleotide having a predetermined sequence is provided. The device can include a support having a plurality of features, each feature having a plurality of oligonucleotides, and within each feature each of the plurality of oligonucleotides including an identical predetermined subunit sequence of X nucleosides and a degenerate sequence of Y nucleosides. In some embodiments, X is between 2 and 50 nucleosides. More particularly, X is between 3 and 20 nucleosides. In some examples, X is 3, 4, 5, 6, 7, 8, 9, or 10 nucleosides. In certain embodiments, Y is between 5 and 100 nucleosides. More particularly, Y is between 5 and 20, or Y is 5, 6, 7, 8, 9, 10, 11, 12, 13, 14, 15, 16, 17, 18, 19, or 20 nucleosides. In some embodiments, the device can have at least $4^X$ different features. In some examples, the device has at least 100, 1,000, 4,000, 10,000 or more different features. The predetermined subunit sequences can be different between the features. A subset of the plurality of the features together can represent the polynucleotide having the predetermined sequence of Z nucleosides. In certain embodiments, at least 10%, 20%, 30%, 40%, 50%, 60%, 70%, 80%, 90%, 95%, 98%, 99% or more of all possible combinations ($4^Z$) of the polynucleotide having the predetermined sequence of Z nucleosides are represented on a single device.

Another aspect of the invention relates to a device for synthesizing at least one polynucleotide having a predetermined sequence on a solid support. In some embodiments, the predetermined sequence includes a subunit sequence. The solid support can have a plurality of spots, and each of the plurality of spots includes a plurality of oligonucleotides having a predetermined subunit sequence. In some embodiments, the plurality of oligonucleotides are covalently linked at their 3' end via a plurality of binding sequences on the solid support. The device further can include a microfluidic member for providing a droplet to a first spot having a first oligonucleotide having a first predetermined subunit sequence to substantially cover the first spot, and the droplet can include one or more reagents that allow one or more of annealing, denaturing, chain extension reaction, ligation, and digestion reaction to produce a first product which includes the first predetermined subunit sequence. The device can also include a member for advancing microfluidic communication between the first spot and a second spot. The second spot has a second predetermined subunit sequence, and at the second spot one or more of annealing, denaturing, chain extension reaction, ligation, and digestion is allowed to produce a second product that includes the first and the second predetermined subunit sequences.

In certain embodiments, the plurality of binding sequences are degenerate sequences having a length of N1 nucleosides, and include up to $4^{N1}$ different sequences within a single spot or feature. In some embodiments, N1 is between 5 and 100 nucleosides. In some embodiments, N1 is between 10 and 50 nucleosides. In some examples, N1 is 5, 6, 7, 8, 9, 10, 11, 12, 13, 14, 15, 16, 17, 18, 19, or 20 nucleosides. In one example, N1 is 10 nucleosides.

In some embodiments, the subunit sequence has a length of N2 and is one of $4^{N2}$ possible sequences. The solid support includes $4^{N2}$ spots or a subset or superset thereof. In some embodiments, N2 is between 2 and 50. In some embodiments, N2 is between 4 and 20. In some examples, N2 is 3, 4, 5, 6, 7, 8, 9, or 10. In one example, N2 is 5.

In some embodiments, the device further includes means for controlling a temperature of the droplet at each of the plurality of spots on the solid support. In certain embodiments, the temperature is controlled at above a predetermined temperature which corresponds to an average annealing temperature of the plurality of binding sequences. In some examples, the temperature is controlled at up to 20° C. above the predetermined temperature. In certain examples, the temperature is controlled at 1, 2, 3, 4, 5, 6, 7, 8, 9, or 10° C. above the predetermined temperature. In some embodiments, the temperature is controlled at above the predetermined temperature such that duplexes, stabilized by a binding agent, remain substantially annealed at said temperature. The binding agent can be a polymerase or a subunit thereof.

In certain embodiments, the droplet contains a primer that at least partially binds to at least one of the plurality of the binding sequences on the first spot, a polymerase or a subunit thereof, and dNTPs or an analog thereof, thereby allowing chain extension off of the primer using the first predetermined subunit sequence as template to produce the first product comprising the first predetermined subunit sequence. The primer can be a plurality of degenerate primers. The first product can serve as a primer for chain extension at the second spot which uses the second predetermined subunit sequence as template to produce the second product comprising the first and the second predetermined subunit sequences.

In some embodiments, the first and the second predetermined subunit sequences are the same or complementary.

In some embodiments, the plurality of oligonucleotides at the 3' end are covalently linked to the plurality of binding sequences via a linker sequence.

A further aspect of the invention includes a device for synthesizing at least one polynucleotide having a predetermined sequence. In some embodiments, the predetermined sequence includes a subunit sequence. The solid support can have a plurality of spots, and each of the plurality of spots can include a plurality of oligonucleotides having a predetermined subunit sequence. The plurality of oligonucleotides are covalently linked at their 3' end via a plurality of binding sequences on the solid support. The plurality of binding sequences can be degenerate sequences having a length of N1 nucleosides and can comprise up to $4^{N1}$ different sequences on the entire device. The device further includes a member for providing a solution to a spot having a first oligonucleotide having a first predetermined subunit sequence. In some embodiment, the spot is substantially covered by the solution. The solution can include one or more reagents that allow one or more of annealing, denaturing, chain extension reaction, ligation, and digestion reaction to produce a product comprising the predetermined subunit sequence.

Other aspects of the invention relate to methods for synthesizing at least one polynucleotide having a predetermined sequence. The polynucleotide can comprise a subunit sequence. In some embodiments, the method includes (a) providing a solid support having a plurality of spots thereon, wherein each of the plurality of spots comprises a plurality of oligonucleotides having a predetermined subunit sequence, wherein the plurality of oligonucleotides are covalently linked at the 3' end via a plurality of binding sequences on the solid support; (b) providing a droplet to a first spot having a first oligonucleotide having a first predetermined subunit sequence, wherein the droplet comprises one or more reagents that allow one or more of annealing, denaturing, chain extension reaction, ligation, and digestion reaction to produce a first product comprising the first predetermined subunit sequence, and (c) advancing microfluidic communication between the first spot and a second spot having a second oligonucleotide having a second predetermined subunit sequence, whereby allowing one or more of annealing, denaturing, chain extension reaction, ligation, and digestion reaction at the second spot to produce a second product comprising the first and the second predetermined subunit sequences.

The method can further include repeating step (c) until the predetermined sequence having the desired subunit sequences is produced. In certain embodiments, the plurality of binding sequences comprises degenerate sequences having a length of N1 nucleosides, and the plurality of binding sequences comprise up to $4^{N1}$ different sequences. In some embodiments, N1 is between 5 and 100. In some embodiments, N1 is between 10 and 50 nucleosides. In some examples, N1 is 5, 6, 7, 8, 9, 10, 11, 12, 13, 14, 15, 16, 17, 18, 19, or 20 nucleosides. In one example, N1 is 10 nucleosides. In some embodiments, the subunit sequence has a length of N2 and is one of $4^{N2}$ possible sequences. The solid support can include $4^{N2}$ spots or a subset or superset thereof. In some embodiments, N2 is between 2 and 50 nucleosides. In some embodiments, N2 is between 4 and 20 nucleosides. In some examples, N2 is 3, 4, 5, 6, 7, 8, 9, or nucleosides. In one example, N2 is 5 nucleosides.

In some embodiments, the method further includes controlling a temperature of the droplet at each of the plurality of spots on the solid support. The temperature can be controlled at above a predetermined temperature which corresponds to an average annealing temperature of the plurality of binding sequences. In some embodiments, the temperature is controlled at up to 20° C. above the predetermined temperature. In some examples, the temperature is controlled at 1, 2, 3, 4, 5, 6, 7, 8, 9, or 10° C. above the predetermined temperature. In certain examples, the temperature is controlled at above the predetermined temperature such that duplexes stabilized by a binding agent remain substantially annealed at said temperature. In one example, the binding agent is a polymerase or a subunit thereof.

In some embodiments, the method further includes providing in the droplet a primer that at least partially binds to at least one of the plurality of the binding sequences on the first spot, a polymerase or a subunit thereof, and dNTPs or analogs thereof, thereby allowing chain extension of the primer using the first predetermined subunit sequence as a template to produce the first product comprising the first predetermined subunit sequence. In some examples, the primer comprises a plurality of degenerate primers.

In various embodiments, the method further includes cleaving the primer to remove unwanted primer sequences from the predetermined sequence. In certain embodiments, the predetermined sequence is amplified via chain extension reactions.

In some embodiments, the method further includes using the first product as a primer for chain extension at the second spot and using the second predetermined subunit sequence as a template to produce the second product comprising the first and the second predetermined subunit sequences.

In various embodiments, one or more of the steps of the method are repeated until a desired amount of the predetermined sequence having the desired subunit sequences is produced.

In another aspect, a method is provided for synthesizing a polynucleotide having a predetermined sequence. The polynucleotide can comprise a subunit sequence. The method includes (a) providing a solid support having a plurality of spots thereon, wherein each of the plurality of spots comprises a plurality of oligonucleotides having a predetermined subunit sequence, wherein the plurality of oligonucleotides at the 3' end are covalently linked via a plurality of binding sequences on the solid support, wherein the plurality of binding sequences are degenerate sequences having a length of N1 nucleosides and comprise up to $4^{N1}$ different sequences; (b) providing a first solution to a first spot having a first plurality of oligonucleotides having a first predetermined subunit sequence, wherein the first solution comprises one or more reagents that allow one or more of annealing, denaturing, chain extension, ligation, and digestion reaction to produce a first product comprising the first predetermined subunit sequence; and (c) providing a second solution to a second spot having a second plurality of oligonucleotides having a second predetermined subunit sequence, wherein the second solution comprises one or more reagents that allow one or more of annealing, denaturing, chain extension reaction, ligation, and digestion reaction to produce a second product comprising the second predetermined subunit sequence. In some embodiment, the first solution and the second solution cover substantially the first and second spot, respectively.

In various embodiments, the first and the second predetermined subunit sequences are different. In some embodiments, the first product serves as a primer for chain extension at the second spot which uses the second predetermined subunit sequence as a template to produce the second product comprising the first and the second predetermined subunit sequences. In certain embodiments, the first and the second predetermined subunit sequences are the same or complementary, and the method further comprises combining the first product and the second product and amplifying therefrom.

Other features and advantages of the devices and methods provided herein will be apparent from the following detailed description, and from the claims. The claims provided below are hereby incorporated into this section by reference. The various embodiments described herein can be complimentary and can be combined or used together in a manner understood by the skilled person in view of the teachings contained herein.

BRIEF DESCRIPTION OF THE DRAWINGS

FIGS. 1A-1F illustrate an exemplary method for the elongation of polynucleotides on a solid support using repeated polymerase extension reactions. FIG. 1A illustrates the addition of a population of free (i.e., non-immobilized) input polynucleotides (element 101) to a first feature of the solid support. FIG. 1B illustrates partial hybridization of polynucleotide sequence (101) to the support-bound oligonucleotide. FIG. 1C illustrates extension of polynucleotide into a longer polynucleotide. FIG. 1D illustrates melting of the extension product (110) from oligonucleotide (106) and release into solution FIG. 1E illustrates the partial annealing of the input polynucleotide (110) due to the complementary sequence region between polynucleotide (110) and oligonucleotide (111) immobilized on a different feature of the solid support. FIG. 1F illustrates the repeated steps of annealing, extension and melting on different features of the solid support.

FIG. 4A illustrates the binding of a construction single-stranded DNA to an oligonucleotide (SEQ ID NO: 2) immobilized on an array. FIG. 4B illustrates the binding of a construction single-stranded DNA to a degenerate base region of the oligonucleotide (SEQ ID NO: 2).

FIG. 6A illustrates a DNA array containing all possible M-mers in N spots. FIG. 6B illustrates hybridization of a universal digestable primer $P_d$ to the universal priming sites $P'_d$ on the array.

FIG. 7A illustrates extension of primers. FIG. 7B illustrates digestion of the digestable primers.

DETAILED DESCRIPTION OF THE INVENTION

Figure 2A:
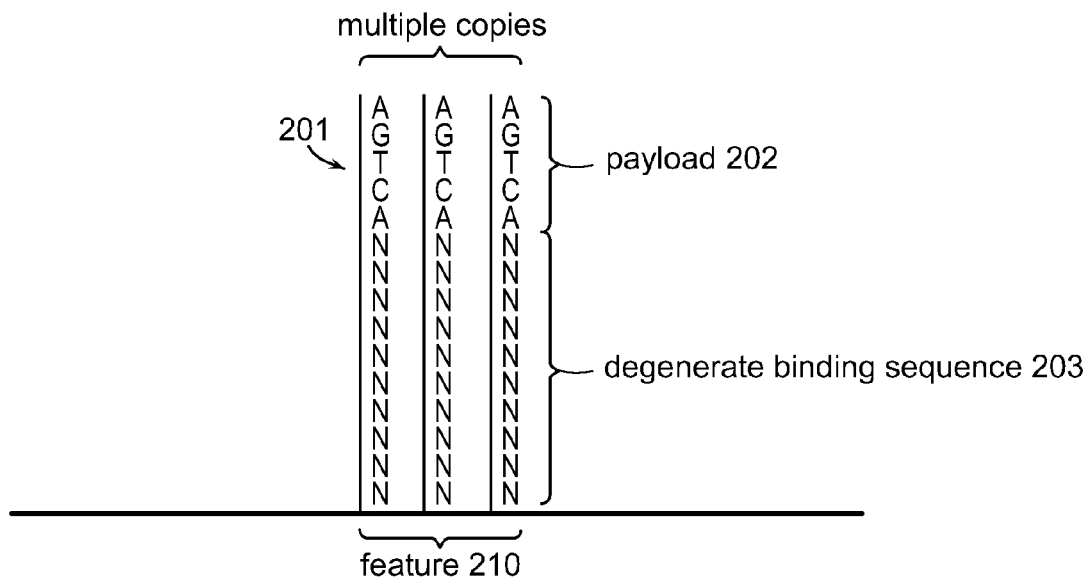
FIG. 2A illustrates an exemplary device having a feature (210) which comprises a plurality of oligonucleotides (201, SEQ ID NO: 1) having a degenerate binding sequence (203) and a payload sequence (202).

Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polynucleotide forms of nucleotides. The oligonucleotides and nucleic acid molecules of the present invention can be formed from naturally occurring nucleotides, for example forming deoxyribonucleic acid (DNA) or ribonucleic acid (RNA) molecules. Alternatively, the naturally occurring oligonucleotides can include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases.

A polymer refers to at least two monomers that are linked together. Biopolymer refers to a polymer found in biological systems comprising a plurality of biological monomeric units or biomonomers linked together, such as nucleic acids (including DNA, RNA, polynucleotides, oligonucleotides, oligonucleotide probes) sugars, proteins, antibodies, antigens, enzymes, coenzymes, ligands, receptors, hormones and labels, and genes that specify any of the above. Biopolymers include compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. As used herein, the term monomer refers to a member of a set of small molecules which are and can be joined together to from an oligomer, a polynucleotide or a compound composed of two or more members. The particular ordering of monomers within a polynucleotide is referred to herein as the "sequence" of the polynucleotide. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polynucleotides such as peptides or polypeptides, polysaccharides, phospholipids, heteropolynucleotides, polyesters, polycarbonates, polyureas, polyamides, polyethyleneimines, polyarylene sulfides, polysiloxanes, polyimides, polyacetates, or any other polynucleotides.

As used herein, the term "predetermined sequence" means that the sequence of the polynucleotide is known and chosen before synthesis or assembly of the polynucleotide. In particular, aspects of the invention is described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotides constructs to be synthesized. In one embodiment, oligonucleotides are short nucleic acid molecules. For example, oligonucleotides can be from 2 to about 10 nucleotides, from 10 to about 30 nucleotides, from 30 to about 50 nucleotides, from 50 to about 100 nucleotides, or more than about 100 nucleotides long. However, shorter or longer oligonucleotides can be used. Oligonucleotides can be designed to have different length.

Oligonucleotides or polynucleotides of any length can be produced by the devices and methods described herein. In some embodiments, the sequence of the desired oligonucleotide or polynucleotide constructs can be divided up into a plurality of shorter sequences that can be synthesized in parallel and/or assembled into a single or a plurality of desired oligonucleotide or polynucleotide constructs using the methods described herein. In some embodiments, the synthesis and/or assembly procedure can include several parallel and/or sequential reaction steps in which a plurality of different nucleic acids or oligonucleotides are synthesized or immobilized, primer-extended, and are combined in order to be assembled (e.g., by extension or ligation as described herein) to generate a longer nucleic acid product to be used for further assembly, cloning, or other applications (see U.S. provisional Application No. 61/235,677 and PCT Application No. PCT/US09/55267, both of which are incorporate herein by reference in their entirety).

Aspects of the invention relate to devices and/or methods for synthesizing at least one polynucleotide having a desired or predetermined sequence on a solid support. The device described herein permits relatively inexpensive, rapid, and high fidelity construction of essentially any polynucleotide desired. Unless defined otherwise below, all technical and scientific terms used herein have the same meaning as commonly understood by one of ordinary skill in the art to which this disclosure belongs. Still, certain elements are defined herein for the sake of clarity. It must be noted that, as used in this specification and the appended claims, the singular forms "a", "an" and "the" include plural referents unless the context clearly dictates otherwise. Thus, for example, reference to "a polynucleotide" can include more than one polynucleotide.

In one aspect, a device for synthesizing a polynucleotide having a predetermined sequence is provided. The device can include a support having a plurality of features, each feature having a plurality of oligonucleotides, and within each feature each of the plurality of oligonucleotides includes an identical predetermined subunit sequence of X nucleosides and a degenerate sequence of Y nucleosides. In some embodiments, X is between 2 and 50. More particularly, X is between 3 and 20. In some examples, X is 3, 4, 5, 6, 7, 8, 9, or 10. In certain embodiments, Y is between 5 and 100. More particularly, Y is between 5 and 20, or Y is 5, 6, 7, 8, 9, 10, 11, 12, 13, 14, 15, 16, 17, 18, 19, or 20. In some embodiments, the device can have at least $4^X$ different features. In some examples, the device has at least 100, 1,000, 4,000, 10,000 or more different features. In some embodiments, the predetermined subunit sequences can be different between each of the features. Yet in other embodiments, the predetermined subunit sequences can be the same. In some embodiments, a subset of the plurality of the features together can represent the polynucleotide having the predetermined sequence of Z nucleosides. In certain embodiments, at least 10%, 20%, 30%, 40%, 50%, 60%, 70%, 80%, 90%, 95%, 98%, 99% or more of all possible combinations ($4^Z$) of the polynucleotide having the predetermined sequence of Z nucleosides are represented on a single device. In some embodiments, any predetermined combination of a subset of the features can be used to produce a polynucleotide of Z nucleosides, such that the device represents at least $4^Z$ different polynucleotides.

Another aspect of the invention relates to a device for synthesizing at least one polynucleotide having a predetermined sequence on a solid support. The predetermined sequence includes a subunit sequence. The solid support has a plurality of spots, and each of the plurality of spots includes a plurality of oligonucleotides having a predetermined subunit sequence. The plurality of oligonucleotides are covalently linked at their 3' end via a plurality of binding sequences on the solid support. The device further includes a member for providing a droplet to a first spot having a plurality of first oligonucleotides having a first predetermined subunit sequence. In some embodiments, the droplet can substantially cover the first spot. The droplet can include one or more reagents that allow one or more of annealing, denaturing, chain extension reaction, ligation, and digestion reaction to produce a first product which includes the first predetermined subunit sequence. The device also includes a member for advancing microfluidic communication between the first spot and a second spot. In some embodiments, the second spot has a second plurality of oligonucleotides having a second predetermined subunit sequence, and at the second spot one or more of annealing, denaturing, chain extension reaction, ligation, and digestion is allowed to produce a second product that includes the first and the second predetermined subunit sequences.

A further aspect of the invention includes a device for synthesizing at least one polynucleotide having a predetermined sequence. The predetermined sequence can include a subunit sequence. In some embodiments, the solid support has a plurality of spots, and each of the plurality of spots includes a plurality of oligonucleotides having a predetermined subunit sequence. The plurality of oligonucleotides are covalently linked at their 3' end via a plurality of binding sequences on the solid support. In some embodiments, the plurality of binding sequences comprises degenerate sequences having a length of N1 nucleosides and comprises up to $4^{N1}$ different sequences on the entire device. The device further includes a member for providing a solution to a spot having a predetermined subunit sequence to substantially cover the spot. The solution includes one or more reagents that allow one or more of annealing, denaturing, chain extension reaction, ligation, and digestion reaction to produce a product comprising the predetermined subunit sequence.

Other aspects of the invention relate to methods for synthesizing at least one polynucleotide having a predetermined sequence. In some embodiments, the at least one polynucleotide sequence comprises a subunit sequence. In some embodiments, the method includes:

(a) providing a solid support having a plurality of spots thereon, wherein each of the plurality of spots comprises a plurality of oligonucleotides having a predetermined subunit sequence, wherein the plurality of oligonucleotides are covalently linked at the 3' end via a plurality of binding sequences on the solid support;

(b) providing a droplet to a first spot having a first plurality of oligonucleotides having a first predetermined subunit sequence, wherein the droplet comprises one or more reagents that allow one or more of annealing, denaturing, chain extension reaction, ligation, and digestion reaction to produce a first product comprising the first predetermined subunit sequence; and (c) advancing microfluidic communication between the first spot and a second spot having a second plurality of oligonucleotides having a second predetermined subunit sequence, whereby allowing one or more of annealing, denaturing, chain extension reaction, ligation, and digestion reaction at the second spot to produce a second product comprising the first and the second predetermined subunit sequences. In some embodiments, the method comprise providing a firs droplet at the first spot and second droplet at the second spot to cover substantially the first and the second spot respectively.

In another aspect, a method is provided for synthesizing at least one polynucleotide having a predetermined sequence. The method includes:

(a) providing a solid support having a plurality of spots thereon, wherein each of the plurality of spots comprises a plurality of oligonucleotides having a predetermined subunit sequence, wherein the plurality of oligonucleotides are covalently linked at the 3' end via a plurality of binding sequences on the solid support, wherein the plurality of binding sequences are degenerate sequences having a length of N1 nucleosides and comprise up to $4^{N1}$ different sequences;

(b) providing a first solution to a first spot having a first plurality of oligonucleotides having a first predetermined subunit sequence to substantially cover the first spot, wherein the first solution comprises one or more reagents that allow one or more of annealing, denaturing, chain extension reaction, ligation, and digestion reaction to produce a first product comprising the first predetermined subunit sequence; and (c) providing a second solution to a second spot having a second plurality of oligonucleotides having a second predetermined subunit sequence to substantially cover the second spot, wherein the second solution comprises one or more reagents that allow one or more of annealing, denaturing, chain extension reaction, ligation, and digestion reaction to produce a second product comprising the second predetermined subunit sequence.

In various embodiments, at least 1,000, at least 10,000, at least 20,000, or at least 30,000 different polynucleotides are synthesized in parallel or sequentially using the device and/or method of the invention. The solid support can be a pin, a rod, a cylinder, a tube, a strip, a slide or the like. Polynucleotides can be synthesized on the entire solid support surface. In some embodiments, polynucleotides can be synthesized on part of the solid support surface in a synthesis area.

In various embodiments, the synthesis area is made of a porous material or of particles of solid material such as beads. The solid support can be composed of glass, silica, plastic, ceramic, beads, metal, organic material, nylon, semiconductor material, oxides or combinations thereof or can be an optical fiber. In some embodiments, the solid support comprises a core member and a synthesis solid surface covering a section of the core member on which polynucleotides are synthesized. The synthesis solid surfaces are interlocked onto the core members via magnetic, mechanical, electrical or chemical mechanisms. In some embodiments, the solid support is magnetized or axially magnetized. The solid supports can be moved independently by electrical, magnetic, electromagnetic, pneumatic, mechanical means or any combination thereof. In a preferred embodiment, the solid supports are moved vertically in relation to the holder and independently of each other.

The synthesis of polynucleotides involves the creation of chemical linkages between monomers. Accordingly, the synthesis of oligonucleotides involves the creation of phosphodiester bonds. The creation of phosphodiester bonds involves a number of sequential chemical steps that can be divided into a number of physical steps. In some embodiments, the different chemical steps are carried out sequentially at the different features or spots designated by the device. The features or spots can be arranged linearly or circularly. Each of these features or spots can have access to a reagent for performing a step of said polynucleotides synthesis. For example, for oligonucleotide synthesis, the features or spots can be accessed by wash reagents, annealing buffer, denaturing buffer, chain extension reaction reagents, ligation reagents, and digestion reagents.

Some aspects of the invention relate to a polynucleotide synthesis/assembly process wherein synthetic oligonucleotides are designed and used as templates for primer extension reactions to produce polynucleotides of desired sequence. During enzymatic amplification or chain extension reactions, an initial step involves the non-covalent binding between a primer sequence and a template sequence to for a duplex. The term "duplex" refers to a nucleic acid molecule that is at least partially double-stranded. A "stable duplex" refers to a duplex that is relatively more likely to remain hybridized to a complementary sequence under a given set of hybridization conditions. In an exemplary embodiment, a stable duplex refers to a duplex that does not contain a base pair mismatch, insertion, or deletion. An "unstable duplex" refers to a duplex that is relatively less likely to remain hybridized to a complementary sequence under a given set of hybridization conditions such as stringent melt. In an exemplary embodiment, an unstable duplex refers to a duplex that is not 100% double-stranded within target sequences, e.g., due to lack of stabilizing agent (e.g., a polymerase or a subunit thereof) under stringent conditions.

Solid Supports

In some embodiments, the methods and provided herein use oligonucleotides that are immobilized on a surface or substrate (e.g., support-bound oligonucleotides). As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), polyvinylidene difluoride (PVDF) membrane, glass, controlled pore glass, magnetic controlled pore glass, ceramics, metals, and the like; either used by themselves or in conjunction with other materials.

In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. In some embodiments, the size of the defined feature is chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

In some embodiments, each solid support comprises a fiber optic emitter/detector, therefore assessing the status of the reaction (e.g. assessing if the solid support is in the reagent when in an activated state). In certain embodiments, each feature or spot on the solid support can be assessed with a fiber optic emitter/detector to assess the status of the reaction for each feature or spot. For example, the status (e.g. activated state or resting state) of each feature or spot can be assessed to determine if the activated solid supports are in contact with the reagent and if the resting solid support are not in contact with the reagent. Similarly, the reaction status can be assessed by electrical measurement. In one embodiment, the solid supports are made of conductive material and can serve as a probe to detect if the solid supports are in contact with a liquid such as a reagent solution. A current flow can be induced in the reagent vessel and the current can then be measured on the solid support side using, for example, an amperometer.

It should be appreciated that the device can include more than one solid supports. In some embodiments, two or more solid supports can be arranged on a solid support holder, with each solid support being monitored by a same or a different emitter/detector. Any arrangement of the solid supports could be employed. In some embodiments, the solid supports are arranged in rows and columns. The holder can comprise one row or one column or a plurality of rows and columns. In some embodiments, the solid supports are arranged in rows and columns and each row and column are equally spaced. For example, the rows can be aligned and/or the columns can be aligned. In other embodiments, rows and/or columns are equally spaced and staggered. Spacing between rows and/or between columns can be variable. In some embodiments, the distance apart two adjacent solid supports is in the range of about 100 µm to 5 mm, usually about 1 to 2 mm. The number of the solid supports comprised in the holder can be variable. In an exemplary embodiment, the holder holds at least 10, at least 100, at least 500, at least 1000, at least 2000 solid supports, at least 5,000, at least 10,000 or at least 50,000 solid supports. In one embodiment, the holder holds 1536 solid supports or pins.

In some embodiments, a vessel corresponding to each feature/spot or the entire solid support contains the reagents or the washing solution. Vessels can be adapted to the solid support dimension and shape. Each step in the synthesis can be carried simultaneously in the same vessel. In one embodiment where more than one solid support is used, at each step of the synthesis, all activated solid supports can be in fluid communication with each others. In other embodiments, the vessels can be microtiter plates and at each or some of the step of the synthesis, the activated solid supports are not in fluid communication with each others. In some embodiments, the vessels can be chilled or heated. One should appreciate that by making use of a plurality of the surface synthesis areas simultaneously, one can minimize the volume of the reagents in the vessels (for example the washing and coupling steps in oligonucleotide synthesis) and therefore minimize the cost of the overall polynucleotide synthesis. The elution step can be performed in a different type of vessel. For example, the elution step can be carried out either by batch elution (i.e. in a same vessel) or by eluting in independent vessels (e.g., wells of a microtiter plate of the like).

Degenerate Binding Sequences

In various embodiments, within each feature on the solid support, each of the plurality of oligonucleotides includes an identical predetermined subunit sequence of X nucleosides and a degenerate sequence of Y nucleosides. In general, a sequence is called degenerate if some of its positions have several possible bases. Assuming $\Sigma=\{T, C, A, G\}$ is the DNA alphabet, a sequence (e.g. a primer) can be shown as $S = x_1 x_2 \ldots x_l$, where $x_i \subseteq \Sigma$, $x_i \neq \emptyset$ and l is the length of S. For example, in the primer $P^* = \{G\} \{G\} \{C,G\} \{A\} \{T,C,G\} \{A\}$ the third position is C or G and the fifth is C, T or G. The IUPAC illustration of $P^*$ will be GGSABA. The degeneracy of a sequence is the number of unique sequence combinations it contains, which can be calculated as $d(S) = \pi^l_{i=1} |x_i|$. For example, $d(P^*) = 1 \times 1 \times 2 \times 1 \times 3 \times 1 = 6$. Degenerate primers are useful for amplifying several related genomic or cDNA sequences, and have been exploited in various applications such as amplifying DNA sequences of homologous genes or genes from a particular protein family and analysis of species diversity. Generally, degenerate PCR can be useful in identifying new members of a gene family or orthologous genes from different organisms. In some embodiments, PCR methods using degenerate primers to amplify unknown DNA sequences that are related to a known DNA sequence or to amplify a mixture of related sequences in one PCR reaction, can be used. Degenerate primers can be a mix of primers with similar sequences.

In various embodiments, degenerate binding sequences can be used to improve the tolerance of a chain extension reaction such that any given primer (or any single-stranded oligonucleotide with a free 3'-OH group) can bind to the degenerate binding sequence and allow extension off of the primer therefrom. The primer can have a specific sequence. The primer can also have any degree of degeneracy. For example, a specific primer P (e.g., having a linker or adapter sequence) can be introduced to a first feature $F_1$ having a first predetermined subunit sequence $X_1$ (e.g., a payload). The primer can anneal to the degenerate binding sequence and extend therefrom using the first predetermined subunit sequence $X_1$ as template, thereby producing a first product having the sequence of $P-X_1$. The first product can be removed from the first feature $F_1$ and introduced to a second feature $F_2$ having a second predetermined subunit sequence $X_2$. At the second feature $F_2$, $P-X_1$ can anneal to the degenerate binding sequence and extend therefrom using the second predetermined subunit sequence $X_2$ as template, thereby producing a second product having the sequence of $P-X_1-X_2$. These steps can be repeated n times until the desired product $P—X_1-X_2-X_3 \ldots -X_n$ is produced. The number n can be any integral, e.g., 1, 2, 3, 4, 5, 6, 7, 9, 10, 15, 20, 25, 30, or more. In some embodiments, features $F_1, F_2, \ldots F_n$ have fixed positions on the solid support (e.g., a universal array or omni chip) and a droplet containing the reaction reagents can be moved around or advanced from one feature to another via automated means. In other embodiments, features $F_1, F_2, \ldots F_n$ can be rearranged (e.g., sequentially) such that all desired predetermined subunit sequences $X_1, X_2, \ldots X_n$ are grouped and manipulated together.

The unwanted primer sequence can then be removed to produce $X_1$-$X_2$-$X_3 \ldots$ -$X_n$ (e.g., by cleaving P off via the linker or adapter sequence therein). Alternatively, a pair of primers that are specific to the $X_1$-$X_2$-$X_3 \ldots$-$X_n$ sequence can be used to specifically amplify $X_1$-$X_2$-$X_3 \ldots$ -$X_n$. It should be understood that amplification of any intermediate product (e.g., $X_1$-$X_2$-$X_3$) can also be used to increase the amount of desired molecules at any step of such sequential synthesis. The amplified intermediate product (e.g., $X_1$-$X_2$-$X_3$) can then be subject to the next extension reaction (e.g., to produce $X_1$-$X_2$-$X_3$-$X_4$). In some embodiments, before the next extension reaction, the amplified intermediate product (e.g., $X_1$-$X_2$-$X_3$) can be additionally subject to a selection process to select for the proper plus or minus strand (e.g., by denaturing the double-stranded molecules and hybridizing to a selection array).

In an exemplary embodiment, a primer/primer binding site that contains a binding and/or cleavage site for a type IIs restriction endonuclease may be used to remove the unwanted primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

In some embodiments, X is between 2 and 50 nucleosides. More particularly, X is between 3 and 20. In some examples, X is 3, 4, 5, 6, 7, 8, 9, or 10. In certain embodiments, Y is between 5 and 100. More particularly, Y is between 5 and 20, or Y is 5, 6, 7, 8, 9, 10, 11, 12, 13, 14, 15, 16, 17, 18, 19, or 20. In some embodiments, the device can have at least $4^X$ different features. In some examples, the device has at least 100, 1,000, 4,000, 10,000 or more different features. The predetermined subunit sequences can be different between the features. A subset of the plurality of the features together can represent the polynucleotide having the predetermined sequence of Z nucleosides. In certain embodiments, at least 10%, 20%, 30%, 40%, 50%, 60%, 70%, 80%, 90%, 95%, 98%, 99% or more of all possible combinations ($4^Z$) of the polynucleotide having the predetermined sequence of Z nucleosides are represented on a single device.

In certain embodiments, the plurality of binding sequences are degenerate sequences having a length of N1 nucleosides, and the plurality of binding sequences comprise up to 4N1 different sequences. In some embodiments, N1 is between 5 and 100. In some embodiments, N1 is between 10 and 50. In some examples, N1 is 5, 6, 7, 8, 9, 10, 11, 12, 13, 14, 15, 16, 17, 18, 19, or 20. In one example, N1 is 10. In some embodiments, the subunit sequence has a length of N2 and is one of $4^{N2}$ possible sequences. The solid support includes $4^{N2}$ spots or a subset or superset thereof. In some embodiments, N2 is between 2 and 50. In some embodiments, N2 is between 4 and 20. In some examples, N2 is 3, 4, 5, 6, 7, 8, 9, or 10. In one example, N2 is 5.

With reference to FIG. 2A, an exemplary device having a feature (210) which comprises a plurality of oligonucleotides (201) having a degenerate binding sequence (203) and a payload sequence (202) is illustrated. The feature can contain multiple copies of oligonucleotides (e.g., $10^3$, $10^4$, $10^5$, $10^6$, $10^7$, etc.). A plurality of features exists on a solid support, and the number of features can be between, e.g., 1 to 100,000,000. In this example, the payload sequence (202) (a predetermined subunit sequence) is 5 nucleoside long (AGTCA) and the degenerate binding sequence (203) is 10 nucleosides long (NNNNNNNNNN) Therefore, to synthesize, e.g., a predetermined 60-mer starting with AGTCA, a total of 12 different features (each having a specific 5-mer payload sequence) can be selected, and an automated path starting from the feature having the AGTCA payload is determined. Then a droplet containing the reaction reagents can be moved around or advanced from one feature to the next via automated means. The droplet, after running through the 12 selected features (a run), contains the desired product (the predetermined 60-mer).

In some embodiments, to increase output, multiple runs through the same predetermined path can be used to produce multiple copies of the desired product. The runs can proceed consecutively, with a first run one or more steps ahead of a second run. Multiple runs can also be manipulated simultaneously, e.g., on multiple solid supports in parallel.

Polynucleotide Synthesis/Assembly

In one aspect, the invention relates to a method for producing high fidelity polynucleotides on a solid support. The synthetic polynucleotides are at least 2, 3, 4, 5, 8, 10, 15, 20, 25, 30, 40, 50, 75, or 100 nucleosides in length, or longer. In exemplary embodiments, a composition of synthetic polynucleotides contains at least about 1%, 2%, 3%, 4%, 5%, 6%, 7%, 8%, 9%, 10%, 15%, 20%, 25%, 50%, 60%, 70%, 80%, 90%, 95% or more copies that have a desired sequence that does not deviate from a predetermined sequence. In certain embodiments, at least 10%, 20%, 30%, 40%, 50%, 60%, 70%, 80%, 90%, 95%, 98%, 99% or more of all possible combinations ($4^Z$) of the polynucleotide having the predetermined sequence of Z nucleosides are represented on a single device.

Some aspects the invention relate to the design of oligonucleotides for high fidelity polynucleotide assembly. Aspects of the invention may be useful to increase the throughput rate of a nucleic acid assembly procedure and/or reduce the number of steps or amounts of reagent used to generate a correctly assembled nucleic acid. In certain embodiments, aspects of the invention may be useful in the context of automated nucleic acid assembly to reduce the time, number of steps, amount of reagents, and other factors required for the assembly of each correct nucleic acid. Accordingly, these and other aspects of the invention may be useful to reduce the cost and time of one or more nucleic acid assembly procedures.

In some embodiments, the method includes synthesizing a plurality of oligonucleotides or polynucleotides in a chain extension reaction using a plurality of single stranded oligonucleotides as templates. As noted above, the oligonucleotides may be first synthesized onto a plurality of discrete features of the surface, or may be deposited on the plurality of features of the support. The support may comprise at least 100, at least 1,000, at least $10^4$, at least $10^5$, at least $10^6$, at least $10^7$, at least $10^8$ features. In a preferred embodiment, the oligonucleotides are covalently attached to the support. In preferred embodiments, the first plurality of oligonucleotides is immobilized to a solid surface. In a preferred embodiment, each feature of the solid surface comprises a high density of oligonucleotides, each oligonucleotide having a different predetermined sequence (e.g., approximately $10^6$-$10^8$ molecules per feature).

In some embodiments, pluralities of different single-stranded oligonucleotides immobilized at different features of a solid support. In some embodiments the oligonucleotides may be attached through their 5' end. In a preferred embodiment, the oligonucleotides are attached through their 3' end. It should be appreciated that by 3' end, it is meant the sequence downstream to the 5' end and by 5' end it is meant the sequence upstream to the 3' end. For example, an oligonucleotide may be immobilized on the support via a nucleotide sequence (e.g., a degenerate binding sequence), linker or spacer (e.g., a moiety that is not involved in hybridization). In some embodiments, the first plurality of oligonucleotides has a 3' end that is complementary to the 3' end of an input single-stranded oligonucleotide. In some embodiments, if the target polynucleotide requires N extension cycles, 1 to N pluralities of different support-bound single stranded oligonucleotides are designed such that collectively the N oligonucleotide sequences comprise the target polynucleotide sequence.

It should be appreciated that different oligonucleotides may be designed to have different lengths. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). Overlapping sequences may be of any suitable length. Overlapping sequences may be between about 5 and about 500 nucleotides long (e.g., between about 10 and 100, between about 10 and 75, between about 10 and 50, about 20, about 25, about 30, about 35, about 40, about 45, about 50, etc.) However, shorter, longer or intermediate overlapping lengths may be used. It should be appreciated that overlaps between different input nucleic acids used in an assembly reaction may have different lengths. In some embodiments, immobilized oligonucleotides include sequence regions having overlapping regions to assist in the assembly of a predetermined nucleic acid sequence. In a preferred embodiment, immobilized oligonucleotides include sequence regions having complementary regions for hybridization to a different oligonucleotide or to a polynucleotide. The complementary regions refer to a sequence region at either a 3' end or a 5' end of the immobilized template oligonucleotide. In a preferred embodiment, the complementary region is localized at the 3' end of the immobilized oligonucleotides. Complementary regions refer to a 3' end or a 5' region of a first oligonucleotide or polynucleotide that is capable of hybridizing to a 5' end or 3' end of a second oligonucleotide or polynucleotide.

FIG. 1 shows an exemplary method for producing polynucleotide on a substrate or solid support. The method comprises several repeated steps of annealing, extension and melting on different features (102, 103, 104, 105) of the solid support (FIG. 1A-1F). With regards to FIG. 1, each feature of the solid support comprises a plurality of molecules (106) having a predefined sequence. In some embodiments, the plurality of molecules having predefined sequences formed the final polynucleotide products. Yet in other embodiment, the plurality molecules having a predefined sequence partially comprise a sequence of the final product.

In some embodiments, a population of free (i.e., non-immobilized) input polynucleotides (element 101, FIG. 1A) is added to a first feature of the solid support (for example feature 102, FIG. 1A). In a preferred embodiment, the input polynucleotides are single stranded polynucleotides (single stranded DNA for example). The input polynucleotide may be a synthetic oligonucleotide that is synthesized or obtained from a commercial supplier. In some embodiments, one or more input nucleic acids may be amplification products (e.g., PCR products), restriction fragments, or other suitable nucleic acid molecules. In some embodiments, the first plurality of oligonucleotides is designed to have a 3' sequence that is complementary to the 3' end of the input polynucleotide. Yet, in other embodiments, the input polynucleotide sequence of (101) is designed such that the 3' a terminal sequence (107) hybridizes to a region (157) of the oligonucleotide sequence (106).

In a first step, the polynucleotide sequence (101) is partially hybridized to the support-bound oligonucleotide, the hybridized region being formed between the (107) region of the polynucleotide and the (157) region of the immobilized oligonucleotide as shown in FIG. 1B. In a second step, polymerase-mediated extension of the hybridized polynucleotides results in a template-based extension of the 3' ends of polynucleotide nucleotides that have annealed 3' regions generating extended polynucleotides containing sequences that are complementary to a sequence region of the template oligonucleotide. Referring to FIG. 1C, the polynucleotide (101) is extended by addition of an appropriate polymerase enzyme and other appropriate components (such as dNTPs, salt, buffer, and etc.) to allow the extension of polynucleotide (101) into a longer polynucleotide (110) that includes sequence (108) that is complementary to sequence (158) of the template oligonucleotide (106). The resulting molecule (110), now elongated by the length of sequence (158) is composed of the sequences of (101) and (108). In a third step, the extension product (110) is melted from oligonucleotide (106) and released into solution (FIG. 1D). The input polynucleotide can then be transferred to a different feature of the support. The input polynucleotide can be transferred or moved mechanically (e.g. pipetting) or using electric, electrostatic, electromagnetic forces. The input polynucleotide (110) can then partially anneal due to the complementary sequence region between polynucleotide (110) and oligonucleotide (111) immobilized on a different feature of the solid support (for example (111), feature (103) of the solid support (100), FIG. 1E)

The annealing of input polynucleotide (110) to oligonucleotide (111), followed by its extension as described above, leads to a longer polynucleotide (120) comprising sequences of polynucleotide (101) and complementary sequences of oligonucleotides (106), (111) and (121). With regards to FIG. 1, in region (103), the population of molecules (intended to be identical to 111) is designed with a sequence region (167) that hybridizes to sequence region (108) of polynucleotide (110), forming a hybridized region (112) composed of the sequences of (108) and (167). The addition of a polymerase with other appropriate components (such as dNTPs, salt, buffer, and etc.) allows for the extension of polynucleotide (110) to include sequence (113) using sequence region (168) as template. The resulting molecule (120), now elongated by the length of sequence (168) and is composed of the sequences of (101), (108), and (113). The molecule can be melted from oligonucleotide (111) and released into solution, allowing it to hybridize to a different region (104) of the surface (100) (FIG. 1E). This process can be repeated to allow the elongation of (120) to include sequence region (123) from sequence region (104) and sequence region (133) from region (105), resulting in sequence (140) (FIG. 1F).

These cycles of melting, transferring, annealing and extension may be repeated until the target full length polynucleotide having a predetermined sequence is synthesized, each cycle of polymerase extension extending oligonucleotide pairs with annealed 3' regions. In each cycle, extension results in the addition of sequences complementary to the template oligonucleotide. Each cycle may include a denaturing, transferring, annealing and extension step. However, the extension may occur under the annealing conditions. Accordingly, in one embodiment, cycles of extension may be obtained by alternating between denaturing conditions (e.g., a denaturing temperature) and annealing/extension conditions (e.g., an annealing/extension temperature). However, in some embodiments, progressive extension may be achieved without temperature cycling. For example, an enzyme capable of promoting rolling circle amplification may be used (e.g., TempliPhi). It should be appreciated that several cycles of polymerase extension may be required to assemble a single target polynucleotide containing the sequences of an initial plurality of template oligonucleotides. In some embodiments, the process can be carried out for M steps, where M can be greater than 1, greater than 10, greater than 100, greater than 1,000, greater than 10,000, greater than 100,000. In some embodiments, the number of cycles is equal or superior to the number of immobilized oligonucleotides. A full length product (or predetermined target polynucleotide sequence) may be isolated or purified using a size selection, cloning, selective binding or other suitable purification procedure. In addition, the full length product may be amplified using appropriate 5' and 3' amplification primers.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentRO (exo-) DNA Polymerase (thermophilic DNA polymerases with or without a 3'→5' exonuclease/proofreading activity from *Thermococcus litoralis*; also known as Th polymerase); Deep VentR® DNA Polymerase and Deep VentR® (exo-) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus kodakaraensis* KOD1 DNA polymerase with a 3'→5' exonuclease/proofreading activity, available from Novagen,); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of *Methanopyrus* topoisomerase, with no exonuclease activity, available from Fidelity Systems); TopoTaq HiFi which incorporates a proofreading domain with exonuclease activity; Phusion™ (a *Pyrococcus*-like enzyme with a processivity-enhancing domain, available from New England Biolabs); any other suitable DNA polymerase, or any combination of two or more thereof. In some embodiments, the polymerase can be a SDP (strand-displacing polymerase; e.g., an SDPe—which is an SDP with no exonuclease activity). This allows isothermal PCR (isothermal extension, isothermal amplification) at a uniform temperature. As the polymerase (for example, Phi29, Bst) travels along a template it displaces the complementary strand (e.g., created in previous extension reactions). As the displaced DNAs are single-stranded, primers can bind at a consistent temperature, removing the need for any thermocycling during amplification.

In some embodiments, the first step of the extension reaction uses a primer (or seed primer). In some embodiments, the oligonucleotides may comprise universal (common to all oligonucleotides), semi-universal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially. In a first step, a primer is added and anneals to an immobilized oligonucleotide. In some embodiments, the support bound or immobilized oligonucleotides comprise a primer binding site wherein the primer is complementary to the primer binding site. In the first step, a solution comprising a polymerase, at least one primer and dNTPs is added at a feature of the solid support under conditions promoting primer extension.

One should appreciate that the extension reactions can take place in a single volume that encompasses all of the utilized features (102, 103, 104, 105, ...), or each step can take place in a localized individual volume (e.g. droplet) that contains only the region(s) of interest during a specific elongation step (see U.S. provisional application 61/235,677, U.S. provisional application 61/257,591 filed on Nov. 3, 2009, U.S. provisional applications 61/264,632 and 61/264,641, filed on Nov. 25, 2009 and PCT application PCT/US09/55267, which are incorporate herein by reference in their entirety). In some embodiments, it may be important to control the seed primer (or the first input polynucleotide) concentration. When performing the extension reactions in a single volume (e.g. pooled extension), the extension product at step N, after melted off the surface-bond template, is free to hybridize to any surface-bond extension template such as (N), (N-1), (N-2), . . . all the way down to the first extension template. Indeed, the extension product having complementary sequence to all of the "prior-step" templates will result in side reactions (side hybridizations) and therefore will reduce the concentration of the polynucleotide of interest. In some embodiments, by increasing the concentration of the initial seed primer concentration, it is possible to correct for the side reactions. In an exemplary embodiment, if the support-bound templates have on average C number of oligonucleotides for each feature (i.e. each step of the extension), and M is the number of total extension steps, it is possible to introduce C*M number of seed molecules at the first step to correct for the side reactions.

In some embodiments, only a selected set of oligonucleotides suitable for hydration are hydrated while the remainder of the support remains dry. In one embodiment, each oligonucleotide has a predefined sequence different from the predefined sequence of the oligonucleotide bound to a different feature. In some embodiments, a set of predefined features may be selectively hydrated, thereby providing hydrated oligonucleotides. In another embodiment, the hydrated oligonucleotides are exposed to further processing within a droplet volume. For example, during the steps illustrated by FIGS. 1A, 1B and 1C, only region (102) may be covered by an isolated liquid volume or droplet, the droplet acting as a virtual reaction chamber. The liquid volume (or aqueous phase) may comprise water, buffer, primers, master mix, release chemicals, enzymes, or any combination thereof. For example the solution may be composed of oligonucleotides primer(s), nucleotides (dNTPs), buffer, polymerase and cofactors.

In other embodiments, the solution is an alkaline denaturing solution. Yet, in other embodiments, the solution may comprise oligonucleotides such as complementary oligonucleotides or input polynucleotide. After melting of the extension product (110), the liquid volume or droplet is moved from region (102) to (103), carrying the melted extension products in solution to region (103). This process of moving the liquid volume can be repeated for each extension step of the process.

Other aspects of the invention relate to methods and devices for assembling at least one polynucleotide having a predefined sequence on a support. In one embodiment, a support is provided that comprises at least one feature having a plurality of surface-bound single-stranded oligonucleotides that are in a dry form and suitable for hydration. Each plurality of oligonucleotides is bound to a discrete feature of the support, and the predefined sequence of each plurality of oligonucleotides attached to the feature is different from the predefined sequence of the plurality of oligonucleotides attached to a different feature. At least one feature is hydrated thereby providing hydrated oligonucleotides within a droplet. The support (or part of the support) is then heated to a first melting temperature under a first stringent melt condition thereby denaturing unstable duplexes (e.g., the duplexes not bound by a stabilizing agent). The melted, unextended single-stranded molecules can be removed from the droplet (e.g., by a wash buffer). With the stable duplexes (e.g., the duplexes bound by a stabilizing agent), at least one plurality of oligonucleotides is synthesized in a chain extension reaction on a first feature of the support by template-dependent synthesis. The products of chain extension are subjected to a second round of denaturation (e.g., at a second melting temperature) and the resulting extended, single-stranded oligonucleotides are removed from the support. Alternatively, the melted, unextended single-stranded molecules can remain within the droplet after the first stringent melt; this way after the second round of denaturation the resulting oligonucleotides can include both unextended and extended molecules. This pool of unextended and extended molecules can be subjected to further selection (e.g., PCR, electrophoresis, etc.) to enrich for extended molecules. These steps can be repeated on at least one other feature until the desired length and/or sequence is produced.

A first droplet comprising a first plurality of oligonucleotides can then be combined to a second droplet comprising a second plurality of oligonucleotides, wherein a terminal region of the second plurality of oligonucleotides comprises identical or complementary sequences with a terminal region of the first set of plurality of oligonucleotides and the first and second plurality of oligonucleotides are contacted under conditions that allow one or more of annealing, chain extension, and denaturing. In some embodiments, the first and second droplets are combined by merging the droplets into a second stage droplet. First and/or second droplets can be moved from a first feature to a second feature of the support. In some embodiments, the surface is coated with a low melting-point substance for storage, for example wax, for storage. In some embodiments, the reactions are initiated by heating the surface above the low-melting point. Yet in other embodiments, the reactions are initiated by hydrating the discrete features. In some embodiments, the support is a microfluidic device. Droplet movement may be controlled by the flow rates of the fluid in the device or by electrical, magnetic, mechanical action applied to the droplets. The droplets and/or the fluid within the microfluidic device can be transported and distributed by a variety of forces including electric forces, electrokinetic forces, pressure based flow techniques, capillary forces, thermo-capillary forces, gravitational and centrifugal forces, magnetic field, a mechanical force, including mechanical pressure waves such as sound waves or ultrasound, or an optical induced force or any combination thereof. One should appreciate that isolated volumes may be routed independently in a sequential or highly parallel fashion. Droplets may be routed using electrowetting-based techniques (see for example, U.S. Pat. No. 6,911,132 and U.S. Patent Application 2006/0054503). Electrowetting principle is based on manipulating droplets on a surface comprising an array of electrodes and using voltage to change the interfacial tension. In some embodiments, droplets are moved using a wettability gradient. It has been shown that droplets placed on wettability gradient surfaces typically move in the direction of increasing wettability (see Zielke and Szymczyk, Eur. Phys. J. Special Topics, 166, 155-158 (2009)). In other embodiments, droplets may be moved using a thermal gradient. When placed on a thermal gradient, droplets move from higher temperature locations towards lower temperature locations. Moving droplets using electrowetting, temperature gradients and wettability gradients depends on the liquid (e.g., aqueous, non-aqueous, solute concentration), the size of the droplets and/or the steepness of the gradient.

The manipulation of fluids to form fluid streams of desired configuration, such as discontinuous fluid streams, particles, dispersions, etc., for purposes of fluid delivery, product manufacture, analysis, and the like, is a relatively well-studied art. See for example, WO/2004/002627 which is incorporated herein in its entirety. In some aspects of the invention, microfluidic devices are used to form and manipulate droplets in a co-planar fashion to allow oligonucleotide synthesis. For example, oligonucleotides may be synthesized using a phosphoramidite method. The phosphoramidite method, employing nucleotides modified with various protecting groups, is one of the most commonly used methods for the de novo synthesis of oligonucleotides. Detailed procedures for the phosphoramidite and hydrogen phosphonate methods of oligonucleotide synthesis are described in the following references that are incorporated by reference: U.S. Pat. Nos. 4,500,707; 4,725,677; and 5,047,524. See also for example, methods outlined in Oligonucleotide and Analogs: A practical approach, F. Eckstein, Ed. IRL Press Oxford University and Oligonucleotide synthesis: A practical approach, Gait, Ed. IRL Oxford Press. Synthesis can be performed either through the coupling of the 5' position of the first monomer to the 3' position of the second monomer (3'-5' synthesis) or vive versa (5'-3' synthesis). Briefly, synthesis of oligonucleotides requires the specific formation of a 3'-5' or 5'-3' phosphodiester linkage. In order to form these specific linkages, the nucleophilic centers not involved in the linkage must be chemically protected through the use of protecting group. By "protecting group" as used herein is meant a species which prevents a segment of a molecule (e.g. nucleotide) from undergoing a specific chemical reaction, but which is removable from the molecule following completion of that reaction. For example, the 5' hydroxyl group may be protected by dimethoxitrityl (DMT). During the deblocking reaction, the DMT is removed with an acid, such as thrichloroacetic acid (TeA) or dichloroacetic acid, resulting in a free hydroxyl group. After washing, a phosphoramidite nucleotide is activated by tetrazole, ethylthiotetrazole, dicyanoimidazole, or benzimidazolium triflate, for example, which remove the iPr2N group on the phosphate group. The deprotected 5' hydroxyl of the first base reacts with the phosphate of the second base and a 5'-3' linkage is formed (coupling step). Unbound bases are washed out and 5' hydroxyl group that did not react during the coupling reaction are blocked by adding a capping group, which permanently binds to the free 5' hydroxyl groups to prevent any further chemical transformation of that group (capping step). The oxidation step may be performed before or after the capping step. During oxidation, the phosphite linkage is stabilized to form a much more stable phosphate linkage. The deblocking/coupling/capping/oxidation cycle may be repeated the requisite number of time to achieve the desired length polynucleotide. In some embodiments, coupling can be synchronized on the array or solid support.

In some embodiments, the oligonucleotides synthesis is synthesized using a device that generates emulsion droplets comprising aqueous droplets within immiscible oil. The droplets may comprise an aqueous phase, an immiscible oil phase, and a surfactant and/or other stabilizing molecules to maintain the integrity of the droplet. In some embodiments, mechanical energy is applied, allowing dispersion of a compound into an oil phase to form droplets, each of which contains a single sort of compound. Preferably, the compound is a nucleotide monomer (i.e. A, T or U, G, C). The compounds can be deposited into the oil phase in the form of droplets generated using inkjet printing technology or piezoelectric drop-on-demand (DOD) inkjet printing technology. Each droplet may comprise a different nucleotide monomer (i.e. A, T or U, G, C) in the same aqueous solution. In preferred embodiments, the droplets are uniform in size and contain one nucleotide at a fixed concentration. The droplets can range in size from 0.5 microns to 500 micron in diameter, which correspond to a volume of about 1 picoliter to about 1 nanoliter. Yet in other embodiments, the droplet may comprise a 2-mer, a 3-mer, a 4-mer, a ti-mer or a 7-mer oligonucleotide. In some embodiments, the droplets are deposited onto a substrate such as a microsubstrate, a microarray or a microchip. The terms microsubstrate, microarray and microchip are used interchangeably herein. The droplets may be deposited using a microfluidic nozzle. In some embodiments, the substrate may be subjected to wash, deblocking solution, coupling, capping and oxidation reactions to elongate the oligonucleotide.

In some embodiments, the droplets carrying the nucleotides can be moved using electrowetting technologies. Electrowetting involves modifying the surface tension of liquids on a solid surface using a voltage. Upon application of an electric field (e.g. alternating or direct), the contact angle between the fluid and surfaces can be modified. For example, by applying a voltage, the wetting properties of a hydrophobic surface can become increasingly hydrophilic and therefore wettable. Electrowetting principle is based on manipulating droplets on a surface comprising an array of electrodes and using voltage to change the interfacial tension. In some embodiments, the array of electrode is not in direct contact with the fluid. In some embodiments, the array of electrode is configured such as the support has a hydrophilic side and a hydrophobic side. The droplets subjected to the voltage will move towards the hydrophilic side. In some embodiments, the array or pattern of electrodes is a high density pattern. One should appreciate that to be used in conjunction with the phosphoramidite chemistry, the array of electrodes should be able to move droplets volumes ranging from 1 µL (and less) to 10 µL. Accordingly, aspects of the invention relate to high voltage complementary semi-conductor microfluidic controller. In some embodiments, the high voltage complementary semi-conductor device (HV-CMOS) has an integrated circuit with high density electrode pattern and high voltage electronics. In some embodiments, the voltage applied is between 15V and 30V.

In some embodiments, the entire support or array containing the discrete features is subjected to thermocycling, annealing temperature conditions, stringent melt temperature conditions, or denaturing temperature conditions. Heating and cooling the support can be performed in any thermal cycle instrument. In other embodiments, one or more discrete features are subjected to specific temperature conditions (annealing, extension, wash or melt). Thermocycling of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from a wide spectrum (100 nm to 100,000 nm, i.e., from ultraviolet to infrared). In some embodiments, the feature on which the droplet is spotted comprises an optical absorber or indicator. In some other embodiments, an optical absorbent material can be added on the surface of the droplet. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. Yet in another embodiment, the whole support can be heated and cooled down to allow enzymatic reactions or other temperature sensitive reactions to take place. One method to control the temperature of the surface droplets is by using a scanning optical energy deposition setup. An energy source can be directed by a scanning setup to deposit energy at various locations on the surface of the solid support comprising support-bound molecules. Optical absorbent material can be added on the surface of the solid support or on the surface of droplet. Optical energy source, such as a high intensity lamp, laser, or other electromagnetic energy source (including microwave) can be used. The temperature of the different reaction sites can be controlled independently by controlling the energy deposited at each of the features.

In some embodiments, after extension or amplification, the polymerase may be deactivated to prevent interference with the subsequent steps. A heating step (e.g., high temperature) can denature and deactivate most enzymes which are not thermally stable. Enzymes may be deactivated in presence (e.g., within the droplet) or in the absence of liquid (e.g., dry array). Heat deactivation on a dry support has the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

It should be appreciated that the description of the synthesis/assembly reactions in the context of oligonucleotides is not intended to be limiting. For example, other polynucleotides (e.g., single-stranded, double-stranded polynucleotides, restriction fragments, amplification products, naturally occurring polynucleotides, etc.) may be included in an assembly reaction, along with one or more oligonucleotides, in order to generate a polynucleotide of interest.

Stringent Melt

As used herein the term "stringent" or "stringency" is used in reference to the conditions of temperature, ionic strength, and the presence of other compounds such as organic solvents, under which nucleic acid hybridizations are conducted. Hybridization stringency increases with temperature and/or chemical properties such as the amounts of salts and/or formamide in the hybridization solution during a hybridization process. With "high stringency" conditions, nucleic acid base pairing will occur only between nucleic acid fragments that have a high frequency of complementary base sequences. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex. Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, New York.

Aspects of the invention relate to enhancing nucleic acid synthesis/assembly procedures by using a stringent melt/wash step after annealing of the polynucleotide to the immobilized oligonucleotides through the complementary regions and prior to polymerase extension. Accordingly, aspects of the invention may be useful for increasing the fidelity of a nucleic acid synthesis/assembly reaction (e.g., increasing the proportion of synthesized/assembled nucleic acids that have a desired predetermined polynucleotide or target sequence). In some aspects of the invention, the immobilized oligonucleotides comprise at least two, at least three different and contiguous sequence regions. As illustrated herewith, the stringent melt/wash step allows for the reduction of the extension of unstable duplexes. In some embodiments, the precise, controlled extension that results in the desired/predetermined sequence relies on the difference in melting temperature between stable (or substantially stable) and unstable (or substantially unstable) duplexes. The use of a stringent melt/wash conditions with precisely controlled temperature, allows for the unstably duplexed molecules to be washed away and removed from the reaction sites, achieving the overall goal of high-precision synthesis.

The conditions for stringent melt (e.g., a precise melting temperature) can be determined by observing a real-time melt curve. In an exemplary melt curve analysis, PCR products are slowly heated in the presence of double-stranded DNA (dsDNA) specific fluorescent dyes (e.g., SYBR Green, LCGreen, SYTO9 or EvaGreen). With increasing temperature the dsDNA denatures (melts), releasing the fluorescent dye with a resultant decrease in the fluorescent signal. The temperature at which the dsDNA melts is determined by factors such as nucleotide sequence, DNA length and GC/AT ratio. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available and may be in which G-C stacking interactions, solvent effects, the desired assay temperature and the like are taken into account. Melt curve analysis can detect a single base difference. Methods for accurate temperature control at individual features can be used as disclosed in U.S. Provisional application 61/264,591). In some embodiments, a stringent wash step with a carefully controlled temperature can melt and remove the error-containing input polynucleotides after annealing.

In some embodiments, during the stringent melt/wash step, it is desirable to have a global stringent melt/wash temperature such that stringent melt/wash can be achieved for all of the participating features under the same temperature condition. Accordingly, some aspects of the invention relate to the design of oligonucleotides such as the stringent melt/wash temperature is the same or within a narrow temperature window. For example, the pluralities of oligonucleotides are designed to have a melting temperature that is within 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20° C. In some embodiments, the length of the hybridization step is varied at different features. One should appreciate that by adjusting the hybridization step length, the melting temperature of each of the extension step can be controlled.

In some embodiments, each support-bound oligonucleotide involved in the extension reactions is designed to have each feature's melting temperature (individual stringent melt temperature) tuned towards the same target melting temperature (global stringent melt temperature). The individual stringent melt temperatures can be tuned as close to the global target as it is possible by increasing or decreasing the lengths of the individual junction QC sections. In some cases, it may not be possible to design oligonucleotides which individual stringent melt temperatures is the same as the global stringent melt temperature. In some embodiments, the support-bound oligonucleotides are designed to have an individual melt temperature to be within a defined range to the global stringent melt temperature. In some embodiments, the defined temperature range can be expressed as a temperature deviation from the target global stringent melt temperature, and can be of 0.001, 0.01, 0.1, 0.2, 0.3, 0.4, 0.5, 0.6, 0.7, 0.8, 0.9, 1° C., or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40° C.

In some embodiments, the stringent melt condition includes controlling a temperature of the droplet at each of the plurality of features/spots on the solid support. The temperature can be controlled at above a predetermined temperature which corresponds to an average annealing temperature of the plurality of binding sequences. In some embodiments, the temperature is controlled at up to 20° C. above the predetermined temperature. In some examples, the temperature is controlled at 1, 2, 3, 4, 5, 6, 7, 8, 9, or 10° C. above the predetermined temperature. In certain examples, the temperature is controlled at above the predetermined temperature such that duplexes stabilized by a binding agent remain substantially annealed at said temperature. In one example, the binding agent is a polymerase or a subunit thereof.

Figure 2B:
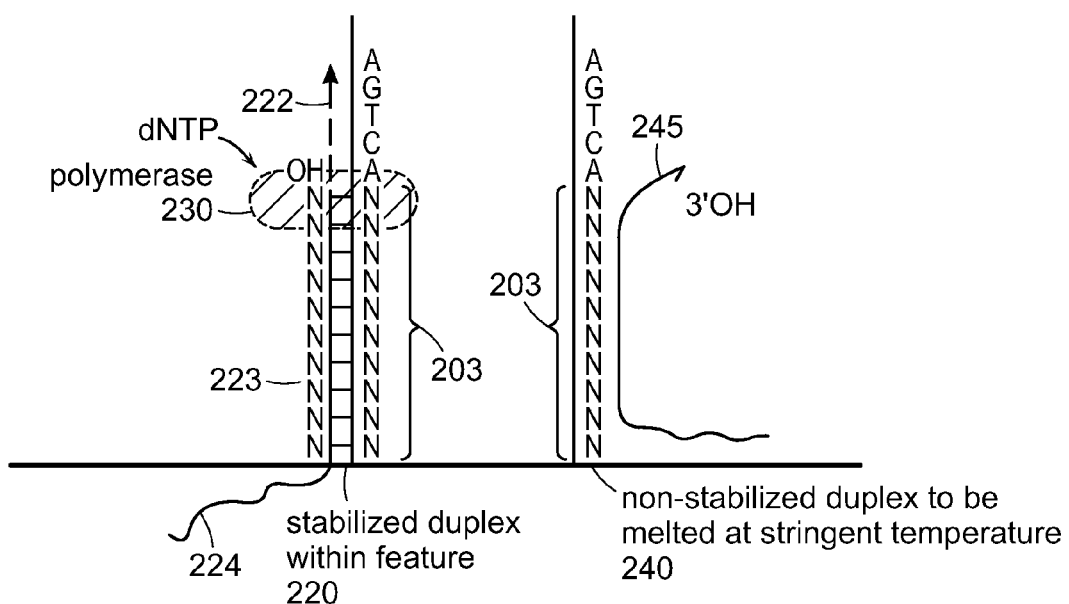
FIG. 2B illustrates under an exemplary stringent melt condition, stabilized duplex (220) proceeding to chain extension while non-stabilized duplex (240) does not.

FIG. 2B illustrates under an exemplary stringent melt condition (e.g., a predetermined temperature), stabilized duplex (220) proceeds to chain extension while non-stabilized duplex (240) does not. The feature contains multiple copies of oligonucleotides having a degenerate binding sequence 203 and supporting a plurality of oligonucleotides. It should be understood that a plurality of features exist on a single solid support, and the number of features can be, e.g., between 1 to 100,000,000. By way of example, FIG. 2B shows two support-bound oligonucleotides (220, 240) attached within the same feature on a solid support. A primer (or any single-stranded oligonucleotide with a free 3'-OH group) in this example has two regions (223, 224) where region 223 (having a specific sequence or any degree of degeneracy) binds to the degenerate binding sequence 203 and allow extension off of the primer therefrom to produce region 222. This is possible because under the stringent melt condition (e.g., the predetermined temperature), those duplexes that can undergo extension reaction (e.g., bound by polymerase) are stable and remain annealed (stabilized duplex 220). On the other hand, the non-stabilized duplexes 240 are only partially annealed to the degenerate binding sequence, thus having an overhang 245 which is not bound by polymerase because its 3'-OH is not available for chain extension. Therefore, non-stabilized duplex 240 is not extended can be removed from the droplet before proceeding to a next feature for further extension.

Automation

It can be advantageous that most of the manipulations be assisted or automated. Such manipulation includes positioning solid support holders or positioning solid support, controlling the temperature of the droplets or vessels containing the reagents, rotating the platforms, controlling the fluid or drain systems, and the like. For example, the positioning of the holder can be suitably controlled by a positioner such as a computer controlled mechanical arm. Alternatively, the holders can be held stationary and the droplets or vessels containing the reagents can be moved by appropriate controllers. Automatic holder or solid support can be connected to, via electronic leads to an electronic control unit. The polynucleotide synthesis device can also include a router for internet connection, a personal computer. The personal compute can control the high level operation of the device through an interface. This operation can comprise the submitting of synthesis jobs and the monitoring of the sequence progression, as well as detecting any fault conditions.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the synthesis/assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Application:

Aspects of the invention may be useful for a range of applications involving the production and/or use of synthetic nucleic acids. As described herein, the invention provides methods for producing synthetic nucleic acids with increased fidelity and/or for reducing the cost and/or time of synthetic assembly reactions. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

In some embodiments, methods described herein may be used during the assembly of large nucleic acid molecules (for example, larger than 5,000 nucleotides in length, e.g., longer than about 10,000, longer than about 25,000, longer than about 50,000, longer than about 75,000, longer than about 100,000 nucleotides, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

In one embodiment, the invention provides devices and methods for synthesizing a plurality of polynucleotides. For example, the invention provides devices and methods for synthesizing a library of polynucleotides. In an exemplary embodiment, library polynucleotides are assembled from chemically synthesized oligonucleotides using techniques such as those set forth herein. In some embodiments, methods of synthesizing libraries containing nucleic acids having predetermined sequence variations are provided herein. In some embodiments, libraries of nucleic acids are libraries of sequence variants. Sequence variants can be variants of a single naturally-occurring protein encoding sequence. However, in some embodiments, sequence variants can be variants of a plurality of different protein-encoding sequences.

Preferably, the polynucleotides are assembled in parallel from the chemically synthesized oligonucleotides. For example, in one embodiment, libraries can be constructed by hybridization based oligonucleotide assembly of overlapping complementary oligonucleotides (see e.g., Zhou et al., *Nucleic Acids Res.*, 32: 5409-5417 (2004); Richmond et al., *Nucleic Acids Res.* 32: 5011-5018 (2004); Tian et al. *Nature* 432: 1050-1054 (2004); and Carr et al. *Nucleic Acids Res.* 32: e162 (2004)). For example, oligonucleotides having complementary, overlapping sequences can be synthesized in parallel on a solid supports as described herein and then eluted off. The oligonucleotides then self assemble based on hybridization of the complementary regions. This technique permits the production of long molecules of DNA having high fidelity and/or high precision sequences.

In some embodiments, the sequence of the polynucleotide construct can be divided up into a plurality of shorter sequences that can be synthesized in parallel and assembled into a single or a plurality of desired polynucleotide constructs using the methods described herein. In certain embodiments, the oligonucleotides are designed to provide the full sense and antisense strands of the polynucleotide construct. After hybridization of the plus and minus strand oligonucleotides, two double-stranded oligonucleotides are subjected to ligation in order to form a first subassembly product. Subassembly products are then subjected to ligation to form a larger DNA or the full DNA sequence.

Ligase-based assembly techniques can involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase can catalyze a ligation reaction between the 5' phosphate of a first nucleic acid to the 3' hydroxyl of a second nucleic acid if the first and second nucleic acids are annealed next to each other on a template nucleic acid). A ligase can be obtained from recombinant or natural sources. A ligase can be a heat-stable ligase. In some embodiments, a thermostable ligase from a thermophilic organism can be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases can be used (e.g., T4 DNA ligase). A lower temperature ligase can be useful for shorter overhangs (e.g., about 3, about 4, about 5, or about 6 base overhangs) that can not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids can be covalently linked together without using enzymes (e.g., without using a ligase). In some embodiments, non-enzymatic techniques can offer certain advantages over enzyme-based ligations. For example, non-enzymatic techniques can have a high tolerance of non-natural nucleotide analogues in nucleic acid substrates, can be used to ligate short nucleic acid substrates, can be used to ligate RNA substrates, and/or can be cheaper and/or more suited to certain automated (e.g., high throughput) applications.

Non-enzymatic ligation can involve a chemical ligation. In some embodiments, nucleic acid termini of two or more different nucleic acids can be chemically ligated. In some embodiments, nucleic acid termini of a single nucleic acid can be chemically ligated (e.g., to circularize the nucleic acid). It should be appreciated that both strands at a first double-stranded nucleic acid terminus can be chemically ligated to both strands at a second double-stranded nucleic acid terminus. However, in some embodiments, only one strand of a first nucleic acid terminus can be chemically ligated to a single strand of a second nucleic acid terminus. For example, the 5' end of one strand of a first nucleic acid terminus can be ligated to the 3' end of one strand of a second nucleic acid terminus without the ends of the complementary strands being chemically ligated.

Accordingly, a chemical ligation can be used to form a covalent linkage between a 5' terminus of a first nucleic acid end and a 3' terminus of a second nucleic acid end, wherein the first and second nucleic acid ends can be ends of a single nucleic acid or ends of separate nucleic acids. In one aspect, chemical ligation can involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) can promote a template-directed chemical ligation. Examples of chemical reactions can include, but are not limited to, condensation, reduction, and/or photo-chemical ligation reactions. It should be appreciated that, in some embodiments, chemical ligation can be used to produce naturally occurring phosphodiester internucleotide linkages, non-naturally-occurring phosphamide pyrophosphate internucleotide linkages, and/or other non-naturally-occurring internucleotide linkages.

In some embodiments, the process of chemical ligation can involve one or more coupling agents to catalyze the ligation reaction. A coupling agent can promote a ligation reaction between reactive groups in adjacent nucleic acids (e.g., between a 5'-reactive moiety and a 3'-reactive moiety at adjacent sites along a complementary template). In some embodiments, a coupling agent can be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation can be an autoligation reaction that does not involve a separate coupling agent. In autoligation, the presence of a reactive group on one or more nucleic acids can be sufficient to catalyze a chemical ligation between nucleic acid termini without the addition of a coupling agent (see, for example, Xu et al., (1997) Tetrahedron Lett. 38:5595-8). Non-limiting examples of these reagent-free ligation reactions can involve nucleophilic displacements of sulfur on bromoacetyl, tosyl, or iodo-nucleoside groups (see, for example, Xu et al., (2001) Nat. Biotech. 19:148-52). Nucleic acids containing reactive groups suitable for autoligation can be prepared directly on automated synthesizers (see, for example, Xu et al., (1999) Nucl. Acids Res. 27:875-81). In some embodiments, a phosphorothioate at a 3' terminus can react with a leaving group (such as tosylate or iodide) on a thymidine at an adjacent 5' terminus. In some embodiments, two nucleic acid strands bound at adjacent sites on a complementary target strand can undergo autoligation by displacement of a 5'-end iodide moiety (or tosylate) with a 3'-end sulfur moiety. Accordingly, in some embodiments, the product of an autoligation can include a non-naturally-occurring internucleotide linkage (e.g., a single oxygen atom can be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid can be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid can be ligated in a separate reaction containing phosphorylated oligonucleotides corresponding to the strand that is to be ligated and non-phosphorylated oligonucleotides corresponding to the complementary strand. The non-phosphorylated oligonucleotides can serve as a template for the phosphorylated oligonucleotides during a chemical ligation (e.g., using cyanogen bromide). The resulting single-stranded ligated nucleic acid can be purified and annealed to a complementary ligated single-stranded nucleic acid to form the target duplex nucleic acid (see, for example, Shabarova et al., (1991) Nucl. Acids Res. 19:4247-51).

In one aspect, a nucleic acid fragment can be assembled in a polynucleotides-mediated assembly reaction from a plurality of oligonucleotides that are combined and extended in one or more rounds of polynucleotides-mediated extensions. In some embodiments, the oligonucleotides are overlapping oligonucleotides covering the full sequence but leaving single stranded gaps that can be filed in by chain extension. The plurality of different oligonucleotides can provide either positive sequences, negative sequences, or a combination of both positive and negative sequences (e.g. plus and minus strands) corresponding to the entire sequence of the nucleic acid fragment to be assembled. In some embodiments, one or more different oligonucleotides can have overlapping sequence regions (e.g., overlapping 5' regions or overlapping 3' regions). Overlapping sequence regions can be identical (i.e., corresponding to the same strand of the nucleic acid fragment) or complementary (i.e., corresponding to complementary strands of the nucleic acid fragment). The plurality of oligonucleotides can include one or more oligonucleotide pairs with overlapping identical sequence regions, one or more oligonucleotide pairs with overlapping complementary sequence regions, or a combination thereof. Overlapping sequences can be of any suitable length. For example, overlapping sequences can encompass the entire length of one or more nucleic acids used in an assembly reaction. Overlapping sequences can be between about 5 and about 500 nucleotides long (e.g., between about 10 and 100, between about 10 and 75, between about 10 and 50, about 20, about 25, about 30, about 35, about 45, about 50, etc.). However, shorter, longer, or intermediate overlapping lengths can be used. It should be appreciated that overlaps between different input nucleic acids used in an assembly reaction can have different lengths.

EXAMPLES

Universal Polymer Array for Polymer Synthesis

Currently there is great interest in synthesizing DNA polymers which are longer than molecules typically classified as oligomers. These polymers may typically be of the length of 100 bases to 3000 nucleotide bases or longer. In the current art, these longer DNA polymers are constructed from shorter oligonucleotides. In this example, devices and methods for constructing an arbitrary DNA polymer sequence starting with a universal oligomer array are illustrated.

Figure 3A:
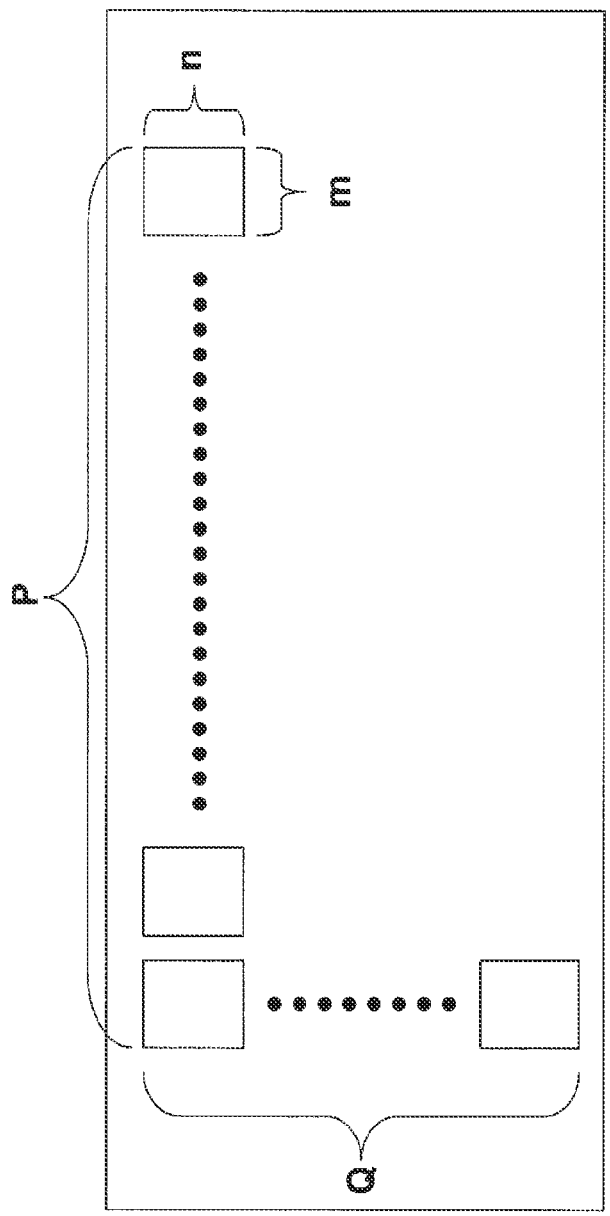
FIG. 3A illustrates an exemplary universal DNA oligomer array with P×Q blocks.
Figure 3B:
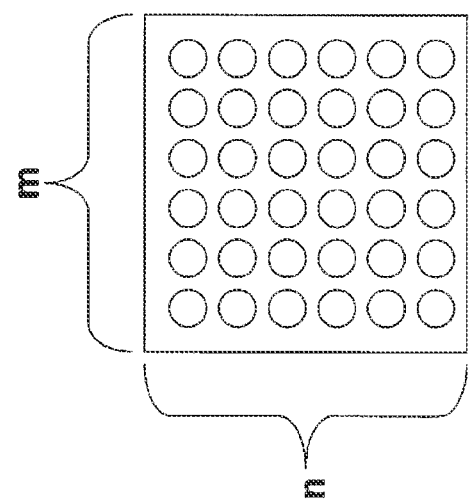
FIG. 3B illustrates each block having m×n oligonucleotide spots or features.

Referring to FIG. 3, a DNA oligomer array is shown in FIG. 3a. P×Q blocks (individual solid supports) are illustrated in which each block has m×n oligonucleotide spots or features (see FIG. 3b). Using a typical array fabrication methodology (e.g. ink jet deposited phosphoramidite chemistries), each spot has on the order of $10^8$ oligonucleotides and may consist of oligonucleotides having a length less than 150 nucleosides. Such an array can also be fabricated by spotting oligonucleotides which have been synthesized off of the surface of the array.

Figure 4A:
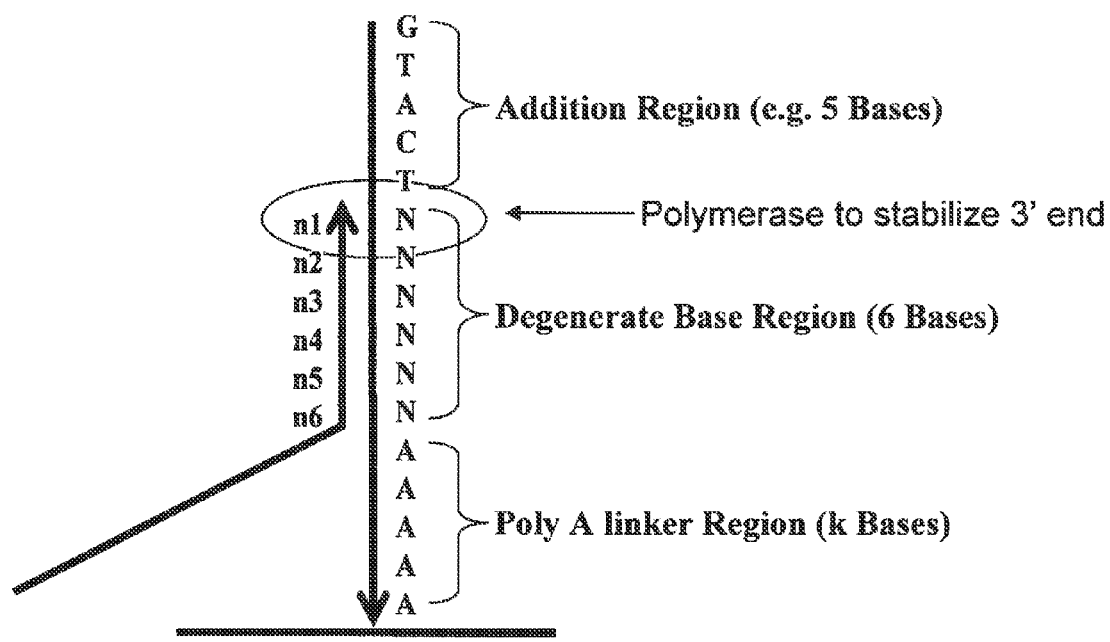
FIGS. 4A-4B illustrate an exemplary binding of a construction single-stranded DNA to an oligonucleotide (SEQ ID NO: 2) immobilized on an array.

FIG. 4A illustrates a construction single-stranded DNA which binds to an oligonucleotide immobilized (e.g. spotted) on an array. The construction single-stranded DNA has at its 3' end a plurality of bases (n1-n6) and can be moved (e.g., by ink jet move) to the spot of interest. The oligonucleotide immobilized (e.g. spotted, SEQ ID NO: 2) on the array has a degenerate base region of 6 bases (N) for binding of nl-n6 sequence of the construction single -stranded DNA. In this example, the oligonucleotide immobilized on the array has a particular set of additional bases (i.e., GTACT) to the 5' end of the degenerate base region. The oligonucleotide can also have k bases of linker region (e.g., poly A) at its 3' end. FIG. 4A illustrates the perfect match situation where nl-n6 anneals well to the degenerate base region. In this situation, a polymerase binds and stabilizes the 3' end. Five additional bases that are complementary to particular set of additional bases of the addition region (i.e., AGTAC) can then be added to the 3' end of the construction single-stranded DNA via chain extension reaction. In an exemplary embodiment, the number of added bases is 5, and $4^5 = 1,024$ separate spots (each having a different 5-mer) can be represented in one array that contains all possible 5mers (1,024 in total). This corresponds to a m x n =32 ×32 spot configuration in ;FIGS. 3A and 3B.

Figure 4B:
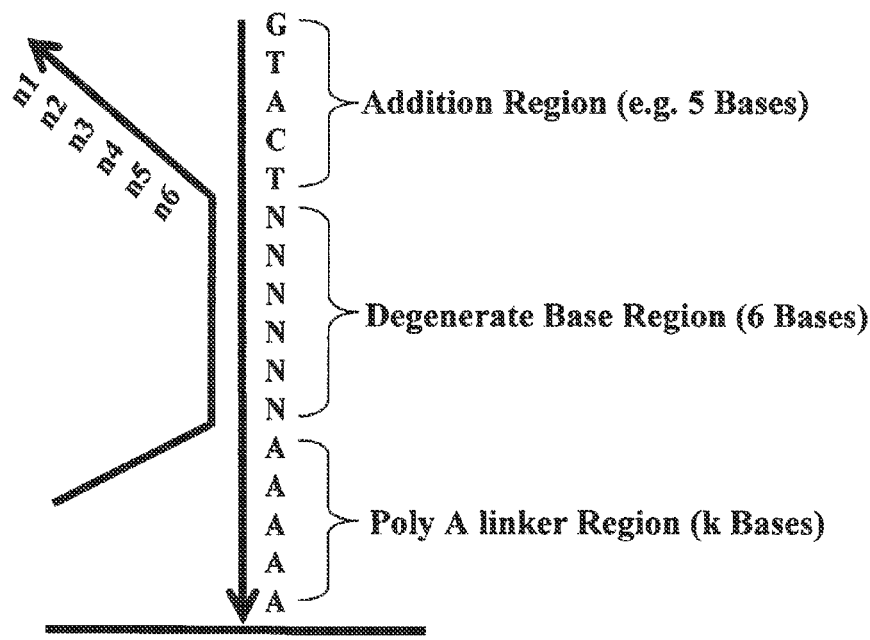

Referring to Figure 4B, it is possible for the degenerate base region to bind the construction single-stranded DNA in a region other than the 3' end (n1-n6). In this situation, the desired set of additional bases would not be added to the 3' end of construction single-stranded DNA even in the presence the addition of polymerase and dNTPs, as the polymerase does not bind. One way to preclude this situation and to increase chain extension reactions, is to hybridize the construction single-stranded DNA to the degenerate base region at a stringent temperature that is slightly above the melting temperature. The addition of the polymerase with dNTPs causes the hybrid or duplex in Figure 4A to become stabilized even under these elevated melting conditions. Without wishing to be bound by theory, one possible explanation is that the polymerase quickly extends the construction single-stranded DNA in this configuration while adding more base pairs and increasing the melting temperature.

Figure 5:
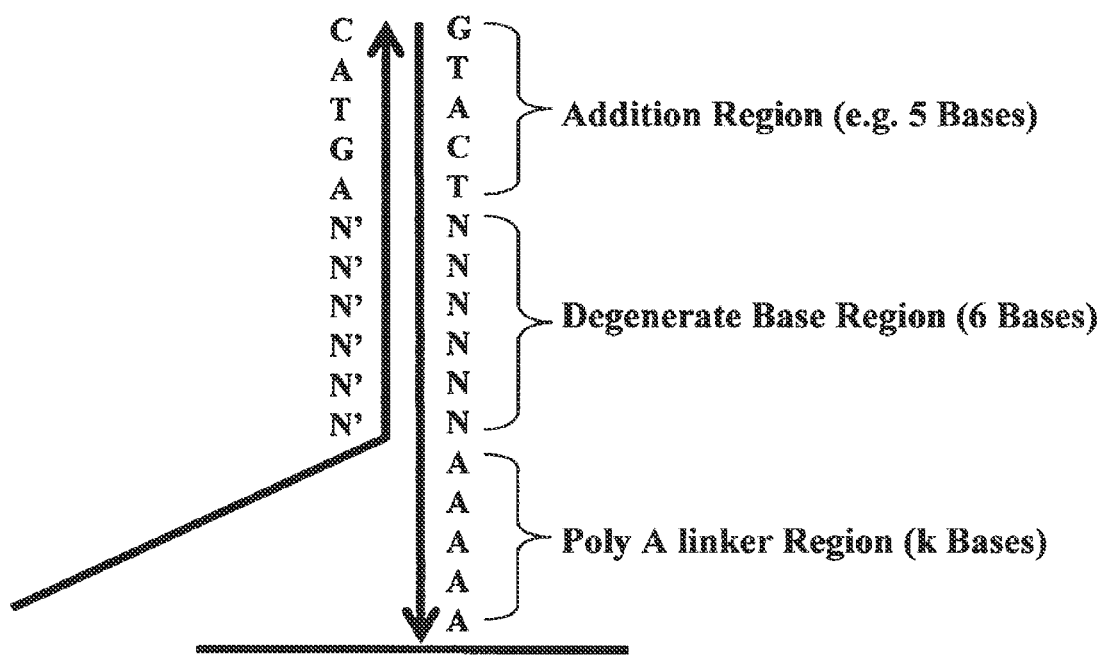
FIG. 5 illustrates the base addition to the construction single-stranded DNA (SEQ ID NO: 3).

FIG. 5 shows the additional set of bases (e.g. AGTAC) being added to the construction single-stranded DNA (SEQ ID NO: 3) under the activity of a polymerase and dNTPs.

Figure 6A:
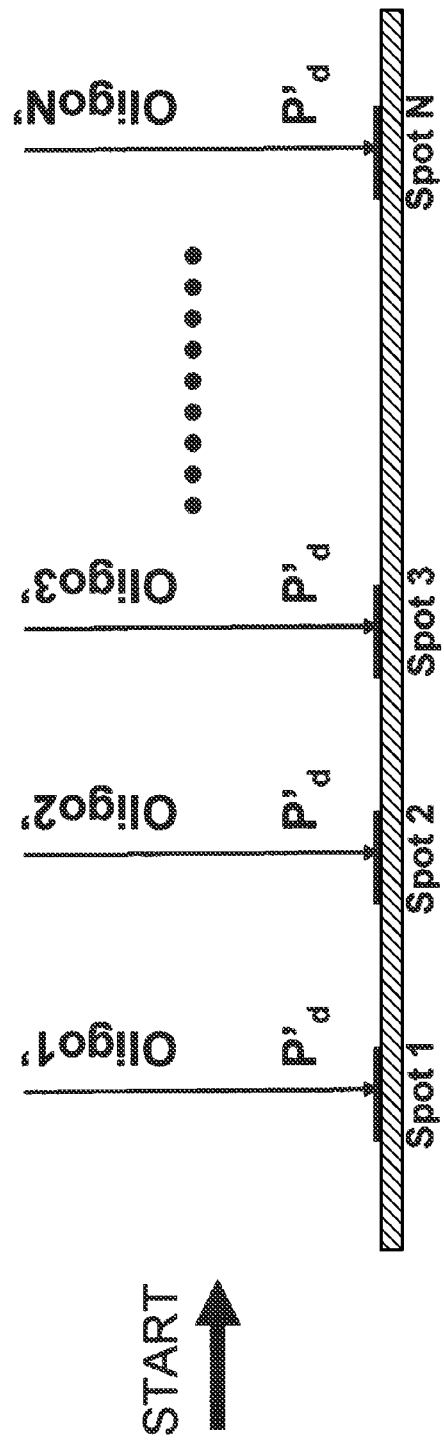
FIGS. 6A-6B illustrate one embodiment for synthesizing a DNA construct from a universal oligomer array.
Figure 6B:
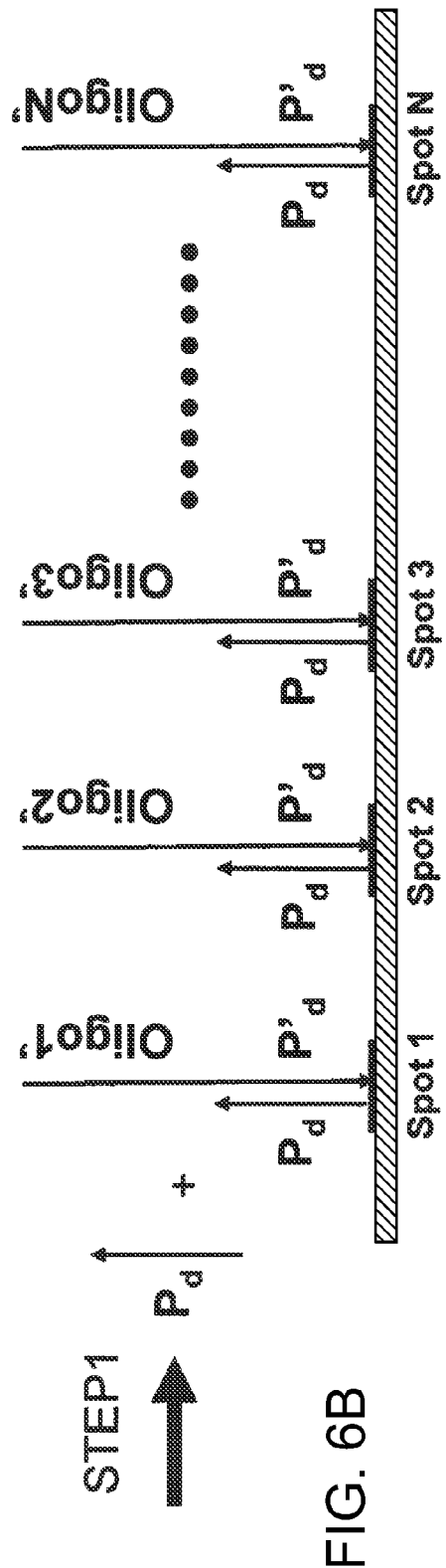

FIGS. 6A, 6B, 7A, 7B and 8 illustrate one embodiment for synthesizing a DNA construct from a universal oligomer array. Referring to FIG. 6A, a DNA array containing all possible M-mers in N spots is provided (either by in situ synthesis or by spotting of oligonucleotides). As an example, when M=10, the array can have N=$4^m$=$4^{10}$ (about $10^6$) spots; this is achievable using for example, current in situ DNA array fabrication techniques. Each oligonucleotide within each spot can be designed to include a universal primer binding site $P'_d$ and an M-mer payload (e.g., Oligo1', Oligo2' OligoN'). Referring to FIG. 6B, at step 1 a universal digestable primer $P_d$ (e.g., containing cleavable uracil groups) is introduced and hybridized to the universal priming sites $P'_d$ on the array.

Figure 7A:
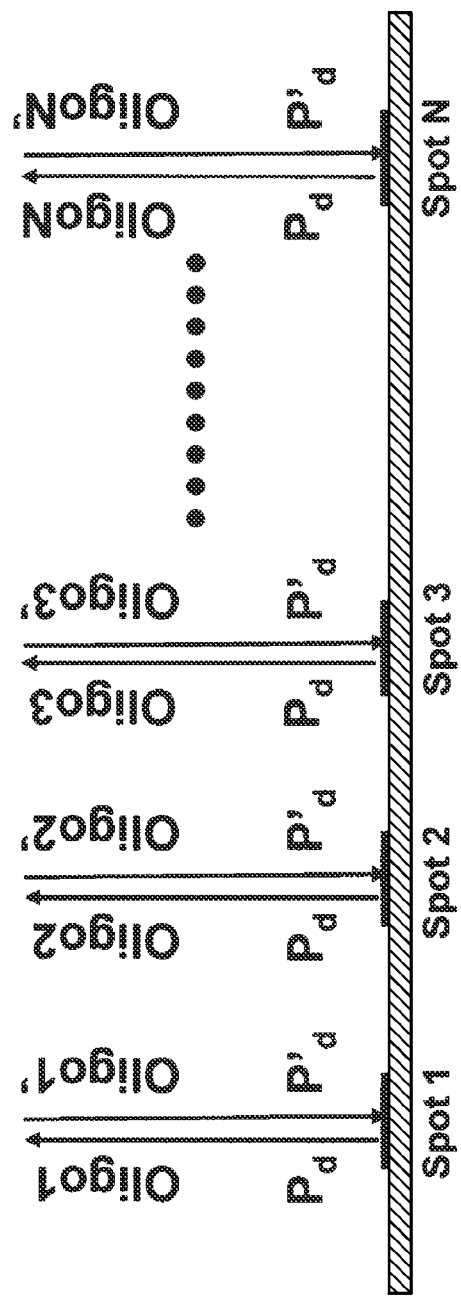
FIGS. 7A-7B illustrate one embodiment for synthesizing a DNA construct from a universal oligomer array.
Figure 7B:
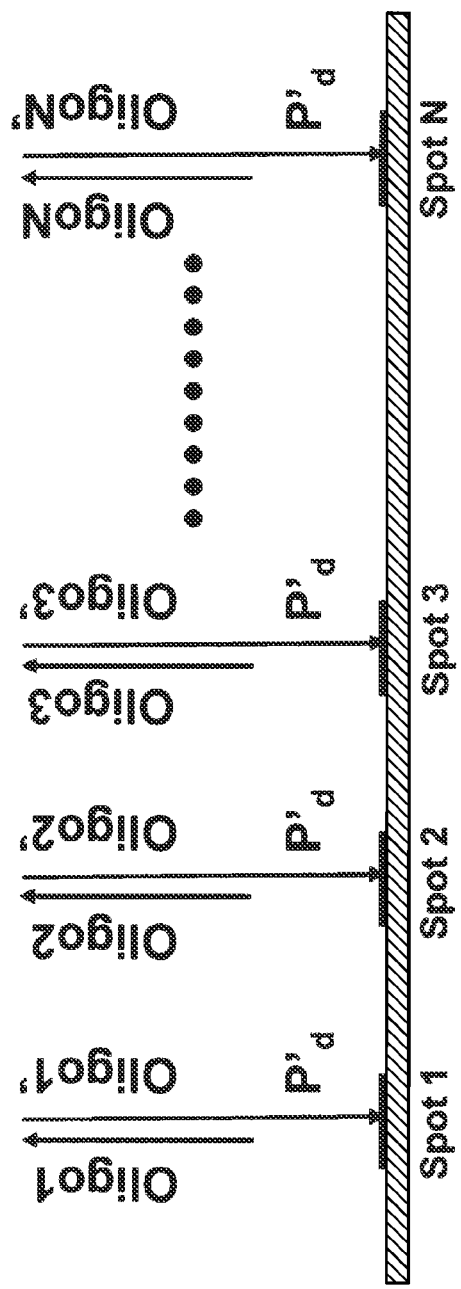

Referring to FIG. 7A, at step 2, the primers $P_d$ are extended using a polymerase and dNTPs, thereby producing $P_d$-Oligo1, $P_d$-Oligo2, $P_d$-Oligo 3, etc. The polymerase can contain a 3'->5' exonuclease activity so as to generate a blunt ended extension product. FIG. 7B illustrates step 3 where the digestable primers $P_d$ are exposed to uracyl deglycosylase, digested and washed away, leaving only the construction oligonucleotides Oligo1, Oligo2, Oligo3, etc.. that remain hybridized at their corresponding spots.

In various embodiments, steps 1-3 can be repeated multiple times. In certain embodiments, any intermediate products can also serve as a primer for further chain extension reactions, thereby producing larger polymers.

Figure 8:
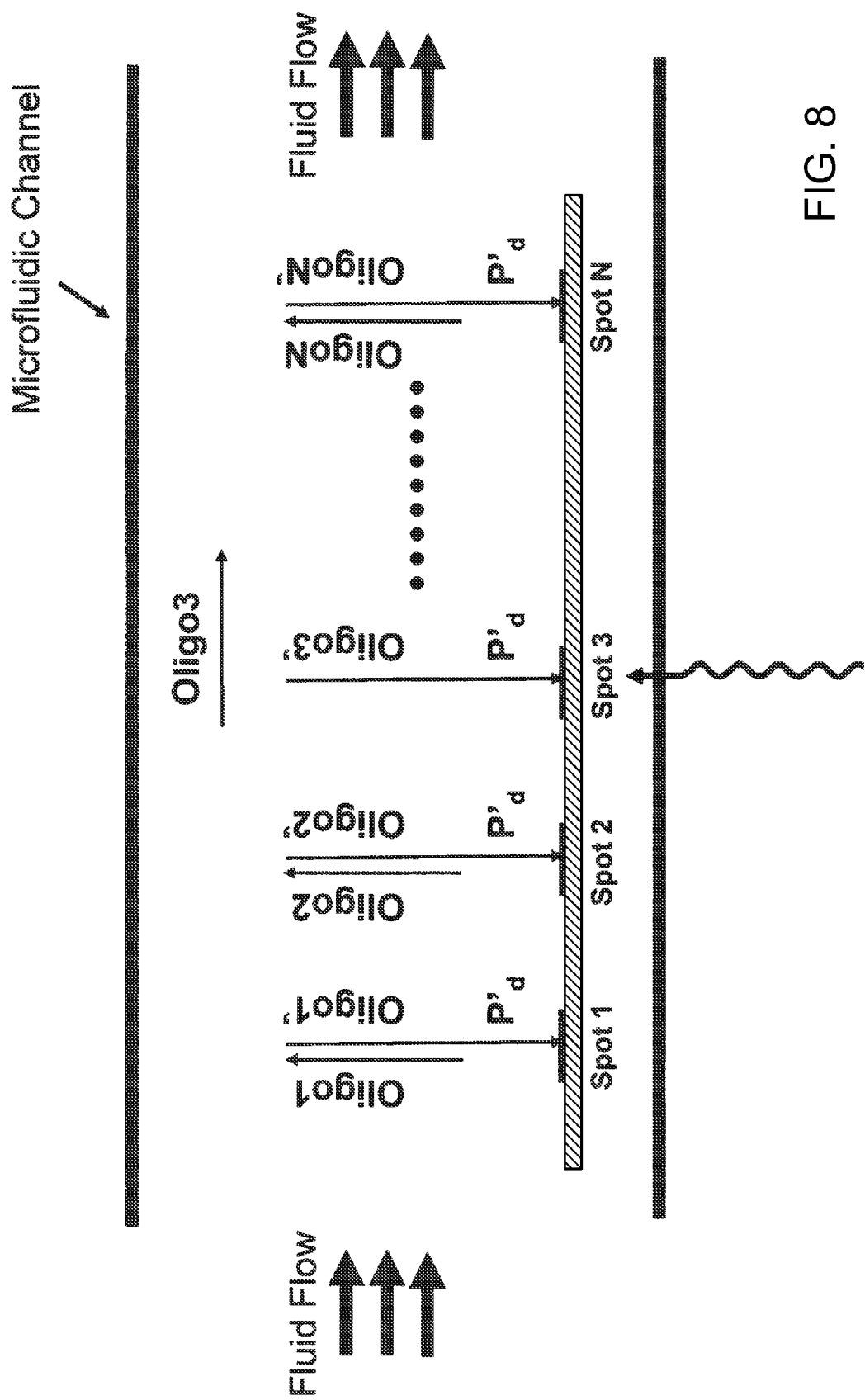
FIG. 8 illustrates an universal DNA array being processed using microfluidic and laser devices.

FIG. 8 illustrates a DNA array being processed by microfluidic and laser devices. The processed DNA array can be placed in a fluidic or microfluidic channel which has a transparent port. Fluid can be flowed or pulsed through the channel and a laser can be used to selectively heat spots thus releasing the corresponding construction oligonucleotides. In this process, the set of construction nucleotides required to build a given DNA sequence by means of standard PCR assembly can be released from the chip into a common pool to carry out a PCR assembly process. The DNA array can also be regenerated by following the steps 1-3 of FIGS. 6 and 7 respectively.

EQUIVALENTS

The present invention provides among other things devices and methods for polynucleotide synthesis. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT application PCT/US09/55267, to U.S. Provisional Application Ser. No. 61/257,591 filed Nov. 3, 2009, to U.S. Provisional Application Ser. No. 61/264,643, entitled "Methods and Apparatus for Chip based DNA error correction", filed on Nov. 25, 2009, U.S. Provisional Application Ser. No. 61/264,632, entitled "Microfluidic devices and methods for gene synthesis", filed on Nov. 25, 2009, U.S. Provisional Application Ser. No. 61/264,641 entitled "Methods and Devices for the Manipulation of Droplets in High Fidelity Polynucleotide Assembly", filed Nov. 25, 2009, U.S. Provisional Application Ser. No. 61/293,192, entitled "Assembly of high fidelity Polynucleotides", filed Jan. 7, 2010, U.S. Provisional Application Ser. No. 61/310,076 entitled "Assembly of high fidelity Polynucleotides", filed on Mar. 3, 2010 and U.S. Provisional Application Ser. No. 61/310,069, entitled "Methods and Microfluidic Devices for the Manipulation of Droplets in High Fidelity Polynucleotide Assembly", filed Mar. 3, 2010. All publications, patents and sequence database entries mentioned herein are hereby incorporated by reference in their entirety as if each individual publication or patent was specifically and individually indicated to be incorporated by reference.

The invention claimed is:

1. A method for synthesizing a target polynucleotide having a predetermined sequence, the method comprising
   (a) providing a solid support having a first feature and a second feature thereon, the first feature having a first plurality of immobilized oligonucleotides each comprising a first predetermined subunit sequence and a first degenerate binding sequence, the second feature having a second plurality of immobilized oligonucleotides each comprising a second predetermined subunit sequence and a second degenerate binding sequence, wherein the first predetermined subunit sequence and the second predetermined subunit sequence together comprise a target polynucleotide;
   (b) generating, in a chain extension reaction using an input oligonucleotide as primer that anneals with the first degenerate binding sequence, a first product comprising the first predetermined subunit sequence at the first feature;
   (c) advancing, via microfluidic communication, the first product to the second feature; and
   (d) generating, in a chain extension reaction using the first product as primer that anneals with the second degenerate binding sequence, a second product comprising the first and the second predetermined subunit sequences at the second feature.

2. The method of claim 1 further comprising
   (i) providing a first solution at the first feature, wherein the first solution comprises the input oligonucleotide and one or more reagents that allow one or more of annealing, denaturing, chain extension, ligation, and digestion reaction to produce the first product; and
   (ii) providing a second solution to the second feature, wherein the second solution comprises one or more reagents that allow one or more of annealing, denaturing, chain extension reaction, ligation, and digestion reaction to produce the second product.

3. The method of claim 1 wherein the first and second degenerate binding sequences are different and each have a length of N1 nucleosides, wherein each degenerate sequence is one of $4^{N1}$ possible sequences.

4. The method of claim 3 wherein N1 is 5, 6, 7, 8, 9, 10, 11, 12, 13, 14, 15, 16, 17, 18, 19, or 20.

5. The method of claim 1 wherein the first and second predetermined subunit sequences each have a length of N2 nucleosides and are one of $4^{N2}$ possible sequences, wherein the solid support comprises $4^{N2}$ spots or a subset or superset thereof.

6. The method of claim 5 wherein N2 is an integer between 2 and 50.

7. The method of claim 1 further comprising individually controlling a temperature at each feature on the solid support, above a predetermined temperature which corresponds to an average annealing temperature of the degenerate binding sequences.

8. The method of claim 7 further comprising controlling the temperature at above the predetermined temperature such that duplexes stabilized by a polymerase or a subunit thereof remain substantially annealed at said temperature.

9. The method of claim 2 further comprising providing in the first solution a polymerase or a subunit thereof, and dNTPs, thereby allowing chain extension of the input oligonucleotide using the first predetermined subunit sequence as a template to produce the first product.

10. The method of claim 9 further comprising cleaving the input oligonucleotide to remove unwanted primer sequences.

11. The method of claim 1 further comprising repeating steps (c) and (d) one or more times until a longer polynucleotide is produced.

12. The method of claim 1 wherein the solid support is positioned in a microfluidic channel.

13. The method of claim 1 wherein the solid support has a plurality of features, a predetermined combination of a subset of which features is used to produce the target polynucleotide.

14. The method of claim 5 wherein N2 is 3, 4, 5, 6, 7, 8, 9, or 10.

15. The method of claim 3 wherein N1 is an integer between 5 and 100.

16. The method of claim 9 wherein the input oligonucleotide contains a site for cleavage by a type IIs restriction endonuclease.

17. The method of claim 16 wherein the type IIs restriction endonuclease is one or more of Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, Psr I, BsmA I, Ple I, Fau I, Sap I, BspM I, SfaN I, Hga I, Bvb I, Fok I, BceA I, BsmF I, Ksp632 I, Eco31 I, Esp3 I, Aar I, Mly I or Btr I.

18. The method of claim 1 wherein the first and second plurality of immobilized oligonucleotides are immobilized via a linker.

\* \* \* \* \*